(12) United States Patent
Coqueron et al.

(10) Patent No.: US 8,318,777 B2
(45) Date of Patent: Nov. 27, 2012

(54) 2-PYRIDINYLETHYLCARBOXAMIDE DERIVATIVES AND THEIR USE AS FUNGICIDES

(75) Inventors: Pierre-Yves Coqueron, Lyons (FR); Philippe Desbordes, Lyons (FR); Darren James Mansfield, Lyons (FR); Heiko Rieck, Sainte-Foy-les-Lyon (FR); Marie-Claire Grosjean-Cournoyer, Curis Au Mont d'Or (FR); Alain Villier, Saint Cyr Au Mont d'Or (FR); Pierre Genix, Lyons (FR)

(73) Assignee: Bayer SAS (FR)

( * ) Notice: Subject to any disclaimer, the term of this patent is extended or adjusted under 35 U.S.C. 154(b) by 0 days.

(21) Appl. No.: 13/303,632

(22) Filed: Nov. 23, 2011

(65) Prior Publication Data
US 2012/0071517 A1    Mar. 22, 2012

Related U.S. Application Data

(60) Division of application No. 12/292,676, filed on Nov. 24, 2008, now Pat. No. 8,071,627, which is a continuation of application No. 10/583,011, filed as application No. PCT/EP2004/014897 on Dec. 16, 2004, now abandoned.

(30) Foreign Application Priority Data

Dec. 19, 2003 (EP) ..................... 03356206

(51) Int. Cl.
*A01N 43/40* (2006.01)
*C07D 401/12* (2006.01)

(52) U.S. Cl. .................. 514/341; 546/276.4; 546/278.4; 546/278.7; 546/279.1

(58) Field of Classification Search .............. 546/276.4, 546/278.4, 278.7, 279.1; 514/341
See application file for complete search history.

(56) References Cited

U.S. PATENT DOCUMENTS

| 3,959,481 A | 5/1976 | Davis et al. ............ 424/285 |
| 5,534,541 A | 7/1996 | Drauz et al. ............ 514/448 |
| 2002/0035279 A1 | 3/2002 | Watanabe et al. ......... 549/549 |

FOREIGN PATENT DOCUMENTS

| EP | 1182199 | 2/2002 |
| EP | 1188752 | 3/2002 |
| JP | 50-10376 B | 4/1975 |
| JP | 63201178 A | 8/1988 |
| JP | 5230016 A | 9/1993 |
| JP | 7112972 A | 5/1995 |
| JP | 8325110 A | 12/1996 |
| JP | 9031069 A | 2/1997 |
| JP | 9176125 A | 7/1997 |
| JP | 2000159610 A | 6/2000 |
| JP | 2000515146 T | 11/2000 |
| JP | 2000336080 A | 12/2000 |
| JP | 2001213869 A | 8/2001 |
| JP | 2001348378 A | 12/2001 |
| JP | 2001348380 A | 12/2001 |
| JP | 2001348381 A | 12/2001 |
| JP | 2001348382 A | 12/2001 |
| JP | 2001348479 A | 12/2001 |
| JP | 2003506465 T | 2/2003 |
| JP | 2003528806 T | 9/2003 |
| WO | WO 96/29871 | 10/1996 |
| WO | WO 98/03495 | 1/1998 |
| WO | WO 00/73290 | 12/2000 |
| WO | WO 01/05769 | 1/2001 |
| WO | WO 01/11965 | 2/2001 |
| WO | WO 01/55124 | 8/2001 |
| WO | WO 03/006456 | 1/2003 |
| WO | WO 2004/074280 | 9/2004 |

OTHER PUBLICATIONS

International Search Report dated May 4, 2005 in corresponding International Application No. PCT/EP2004/014897.

*Primary Examiner* — Patricia Morris
(74) *Attorney, Agent, or Firm* — Ostrolenk Faber LLP

(57) ABSTRACT

The invention discloses a compound of general formula (I)

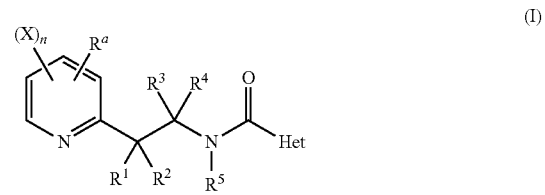

and a process for preparing this compound. The invention discloses a fungicidal composition comprising a compound of general formula (I) and a method for treating plants by applying a compound of general formula (I) or a composition comprising it.

18 Claims, No Drawings

2-PYRIDINYLETHYLCARBOXAMIDE DERIVATIVES AND THEIR USE AS FUNGICIDES

CROSS-REFERENCE TO RELATED APPLICATIONS

This application is a divisional application of U.S. Ser. No. 12/292,676, filed on Nov. 24, 2008, now U.S. Pat. No. 8,071,627, which is a continuation application of U.S. Ser. No. 10/583,011, filed on Oct. 6, 2006, abandoned, which is a 35 U.S.C. §371 national phase conversion of PCT/EP2004/014897, filed on Dec. 16, 2004, which claims priority to European Patent Application 03356206.7, filed Dec. 19, 2003, the entire contents of which are incorporated herein by reference.

The present invention relates to novel N-[2-(2-pyridinyl)ethyl]carboxamide derivatives, their process of preparation, their use as fungicides, particularly in the form of fungicidal compositions, and methods for the control of phytopathogenic fungi of plants using these compounds or their compositions.

International patent application WO 01/11965 discloses a broad family of fungicidal compounds. There is no specific disclosure of N-[2-(2-pyridinyl)ethyl]carboxamide derivatives.

It is always of high-interest in the field of agrochemicals to use pesticidal compounds more active than the compounds already known by the man ordinary skilled in the art whereby less compound can be used whilst retaining equivalent efficacy.

We have now found a new family of compounds which show enhanced fungicidal activity over the general known family of such compounds.

Accordingly, the present invention relates to a N-[2-(2-pyridinyl)ethyl]carboxamide derivative of general formula (I)

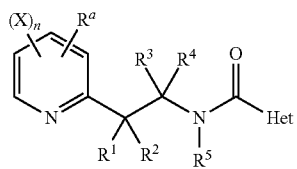

in which:

n is 1, 2 or 3;

$R^a$ is a $C_1$-$C_6$-halogenoalkyl having 1 to 5 halogen atoms;

each substituent X is chosen, independently of the others, as being a hydrogen atom, a halogen atom, a $C_1$-$C_6$-alkyl or a $C_1$-$C_6$-halogenoalkyl;

$R^1$, $R^2$, $R^3$ and $R^4$ are chosen, independently of the others as being a hydrogen atom, a halogen atom, a cyano group, a hydroxy group, an amino group, a sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_6$-alkyl, a $C_2$-$C_6$-alkenyl, a $C_2$-$C_6$-alkynyl, a $C_1$-$C_6$-alkylamino, a di-$C_1$-$C_6$-alkylamino, a $C_1$-$C_6$-alkoxy, a $C_1$-$C_6$-halogenoalkyl having 1 to 5 halogen atoms, a $C_1$-$C_6$-halogenoalkoxy having 1 to 5 halogen atoms, a $C_1$-$C_6$-alkylsulfanyl, a $C_1$-$C_6$-halogenoalkylsulfanyl having 1 to 5 halogen atoms, a $C_2$-$C_6$-alkenyloxy, a $C_2$-$C_6$-halogenoalkenyloxy having 1 to 5 halogen atoms, a $C_3$-$C_6$-alkynyloxy, a $C_3$-$C_6$-halogenoalkynyloxy having 1 to 5 halogen atoms, a $C_3$-$C_6$-cycloalkyl, a $C_3$-$C_6$-halogenocycloalkyl having 1 to 5 halogen atoms, a $C_1$-$C_6$-alkylcarbonyl, a $C_1$-$C_6$-halogenoalkylcarbonyl having 1 to 5 halogen atoms, a $C_1$-$C_6$-alkylcarbamoyl, a di-$C_1$-$C_6$-alkylcarbamoyl, a N—$C_1$-$C_6$-alkyloxycarbamoyl, a $C_1$-$C_6$-alkoxycarbamoyl, a N—$C_1$-$C_6$-alkyl-$C_1$-$C_6$-alkoxycarbamoyl, a $C_1$-$C_6$-alkoxycarbonyl, a $C_1$-$C_6$-halogenoalkoxycarbonyl having 1 to 5 halogen atoms, a $C_1$-$C_6$-alkylcarbonyloxy, a $C_1$-$C_6$-halogenoalkylcarbonyloxy having 1 to 5 halogen atoms, a $C_1$-$C_6$-alkylcarbonylamino, a $C_1$-$C_6$-halogenoalkylcarbonylamino having 1 to 5 halogen atoms, a $C_1$-$C_6$-alkylaminocarbonyloxy, a di-$C_1$-$C_6$-alkylaminocarbonyloxy, a $C_1$-$C_6$-alkyloxycarbonyloxy, a $C_1$-$C_6$-alkylsulphenyl, a $C_1$-$C_6$-halogenoalkylsulphenyl having 1 to 5 halogen atoms, a $C_1$-$C_6$-alkylsulphinyl, a $C_1$-$C_6$-halogenoalkylsulphinyl having 1 to 5 halogen atoms, a $C_1$-$C_6$-alkylsulphonyl, a $C_1$-$C_6$-halogenoalkylsulphonyl having 1 to 5 halogen atoms, a benzyl, a benzyloxy, a benzylsulfanyl, a benzylsulfinyl, a benzylsulfonyl, a benzylamino, a phenoxy, a phenylsulfanyl, a phenylsulfinyl, a phenylsulfonyl, a phenylamino, a phenylcarbonylamino, a 2,6 dichlorophenyl-carbonylamino group or a phenyl group; or $R^1$ and $R^2$ may form together a cyclopropyl, a cyclobutyl, a cyclopentyl or a cyclohexyl;

with the proviso that when three of the four substituents $R^1$, $R^2$, $R^3$ and $R^4$ are a hydrogen atom, then the fourth substituent is not a hydrogen atom;

$R^5$ is chosen as being a hydrogen atom, a cyano group, a formyl group, a hydroxy group, a $C_1$-$C_6$-alkyl, a $C_1$-$C_6$-halogenoalkyl having 1 to 5 halogen atoms, a $C_1$-$C_6$-alkoxy, a $C_1$-$C_6$-halogenoalkoxy having 1 to 5 halogen atoms, a $C_3$-$C_6$-cycloalkyl, a $C_3$-$C_6$-halogenocycloalkyl having 1 to 5 halogen atoms, a $C_2$-$C_6$-alkenyl, a $C_2$-$C_6$-alkynyl, a $C_1$-$C_6$-alkoxy-$C_1$-$C_6$-alkyl, a $C_1$-$C_6$-cyanoalkyl, a $C_1$-$C_6$-aminoalkyl, a $C_1$-$C_6$-alkylamino-$C_1$-$C_6$-alkyl, a di-$C_1$-$C_6$-alkylamino-$C_1$-$C_6$-alkyl, a $C_1$-$C_6$-alkylcarbonyl, a $C_1$-$C_6$-halogenalkylcarbonyl having 1 to 5 halogen atoms, a $C_1$-$C_6$-alkyloxycarbonyl, a $C_3$-$C_7$-cycloalkyl, a $C_3$-$C_7$-halogenocycloalkyl having 1 to 5 halogen atoms, a $C_3$-$C_7$-cycloalkyl-$C_1$-$C_6$-alkyl, a $C_1$-$C_6$-benzyloxycarbonyl, a $C_1$-$C_6$-alkoxy-$C_1$-$C_6$-alkylcarbonyl, a $C_1$-$C_6$-alkylsulfonyl or a $C_1$-$C_6$-halogenoalkylsulfonyl having 1 to 5 halogen atoms; and Het represents a 5-, 6- or 7-membered non-fused heterocycle with one, two or three heteroatoms which may be the same or different, Het being linked by a carbon atom and being at least substituted in ortho position;

as well as its salts, N-oxides, metallic complexes, metalloidic complexes and optically active isomers.

In the context of the present invention:

halogen means fluorine, bromine, chlorine or iodine;
heteroatom means N, O or S;
carboxy means —C(=O)OH;
carbonyl means —C(=O)—;
carbamoyl means —C(=O)NH$_2$;
N-hydroxycarbamoyl means —C(=O)NHOH;
an alkyl group, an alkenyl group, and an alkynyl group as well as moieties containing these terms, can be linear or branched.

In the context of the present invention, it has also to be understood that in the case of di-substituted amino and of di-substituted carbamoyl radicals, the two substituents may form together with the nitrogen atom bearing them a saturated heterocyclic ring containing 3 to 7 atoms.

According to the present invention, the 2-pyridyl may be substituted in every position by $(X)_n$ and $R^a$, in which X, $R^a$ and n are as defined above. Preferably, the present invention relates to N-[2-(2-pyridinyl)ethyl]carboxamide derivative of general formula (I) in which the different characteristics may be chosen alone or in combination as being:

- as regards n, n is 1 or 2. More preferably n is 1.
- as regards X, X is preferably chosen as being a halogen atom. More preferably X is chlorine;
- as regards $R^a$, $R^a$ is preferably chosen as being —$CF_3$;
- as regards the positions in which the 2-pyridyl is substituted, the 2-pyridyl is substituted in 3- and/or in 5-position. More preferably, the 2-pyridyl is substituted in 3-position by X and in 5-position by Y.

Even more preferably, the 2-pyridyl is substituted in 3-position by —Cl and in 5-position by —$CF_3$.

According to the present invention, the two carbon atoms and the nitrogen atom of the "ethylamide part" of the compound of formula (I) are respectively substituted by $R^1$ and $R^2$, $R^3$ and $R^4$, and $R^5$, at least one the substituents $R^1$, $R^2$, $R^3$ and $R^4$ being different from hydrogen. Preferably, the present invention also relates to N-[2-(2-pyridinyl)ethyl]carboxamide derivative of general formula (I) in which the following characteristics may be chosen alone or in combination as being:

- as regards $R^1$ and $R^2$, $R^1$ and $R^2$ may be chosen, independently of each other, as being a hydrogen atom, a halogen atom, a cyano group, a hydroxy group, a $C_1$-$C_6$-alkyl, a $C_1$-$C_6$-halogenoalkyl having 1 to 5 halogen atoms, a $C_2$-$C_6$-alkenyl, a $C_1$-$C_6$-alkoxy, a $C_1$-$C_6$-alkylsulfanyl, a $C_1$-$C_6$-alkylsulfenyl, a $C_1$-$C_6$-alkylsulfinyl, a $C_1$-$C_6$-alkoxycarbonyl, a $C_1$-$C_6$-alkylcarbonylamino, a $C_1$-$C_6$-alkoxycarbonyloxy, a $C_1$-$C_6$-alkoxycarbonylamino or a phenyl group. More preferably, $R^1$ and $R^2$ may be chosen, independently of each other, as being a halogen atom, a $C_1$-$C_6$-alkyl, a $C_1$-$C_6$-halogenoalkyl having 1 to 5 halogen atoms or a $C_1$-$C_6$-alkylcarbonylamino.
- as regards $R^3$ and $R^4$, $R^3$ and $R^4$ may be chosen, independently of each other, as being a hydrogen atom, a halogen atom, a cyano group, a $C_1$-$C_6$-alkyl, a $C_1$-$C_6$-halogenoalkyl having 1 to 5 halogen atoms, a $C_1$-$C_6$-alkylcarbonylamino or a phenyl group. More preferably, $R^3$ and $R^4$ may be chosen, independently of each other, as being a halogen atom, a $C_1$-$C_6$-alkyl, a $C_1$-$C_6$-halogenoalkyl having 1 to 5 halogen atoms or a phenyl group.
- as regards $R^5$, $R^5$ may be chosen as being a hydrogen atom or a $C_3$-$C_7$-cycloalkyl.

According to the present invention, "Het" of the compound of general formula (I) may be a five membered ring heterocycle. Specific examples of compounds of the present invention where Het is a five membered heterocycle include:

Het represents a heterocycle of the general formula (Het-1)

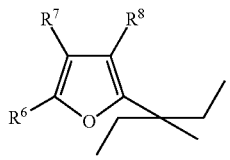

(Het-1)

in which:
$R^6$ and $R^7$ may be the same or different and may be a hydrogen atom, a halogen atom, an amino group, a nitro group, a $C_1$-$C_4$-alkyl or a $C_1$-$C_4$-halogenoalkyl having 1 to 5 halogen atoms; and
$R^8$ may be a halogen atom, a nitro group, a $C_1$-$C_4$-alkyl or a $C_1$-$C_4$-halogenoalkyl having 1 to 5 halogen atoms.

Het represents a heterocycle of the general formula (Het-2)

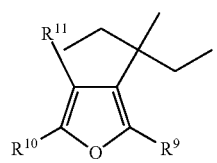

(Het-2)

in which:
$R^9$ may be a hydrogen atom, a halogen atom, a $C_1$-$C_4$-alkyl or a $C_1$-$C_4$-halogenoalkyl having 1 to 5 halogen atoms; and
$R^{10}$ and $R^{11}$ may be the same or different and may be a hydrogen atom, a halogen atom, an amino group, a $C_1$-$C_4$-alkyl or a $C_1$-$C_4$-halogenoalkyl having 1 to 5 halogen atoms;
provided that the $R^9$ and $R^{11}$ are not both a hydrogen atom.

Het represents a heterocycle of the general formula (Het-3)

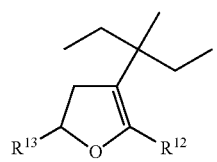

(Het-3)

in which:
$R^{12}$ may be a halogen atom, a $C_1$-$C_4$-alkyl or a $C_1$-$C_4$-halogenoalkyl having 1 to 5 halogen atoms; and
$R^{13}$ may be a hydrogen atom, a $C_1$-$C_4$-alkyl or a $C_1$-$C_4$-halogenoalkyl having 1 to 5 halogen atoms.

Het represents a heterocycle of the general formula (Het-4)

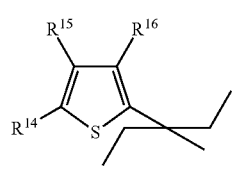

(Het-4)

in which:
$R^{14}$ and $R^{15}$ may be the same or different and may be a hydrogen atom, a halogen atom, a $C_1$-$C_4$-alkyl, a $C_1$-$C_4$-halogenoalkyl having 1 to 5 halogen atoms, a $C_1$-$C_4$-alkylthio, a $C_1$-$C_4$-alkylsulphonyl, a phenyl optionally substituted by a halogen atom or a $C_1$-$C_4$-alkyl or a pyridyl optionally substituted by a halogen atom or a $C_1$-$C_4$-alkyl; and
$R^{16}$ may be a halogen atom, a cyano group, a $C_1$-$C_4$-alkyl, a $C_1$-$C_4$-halogenoalkyl having 1 to 5 halogen atoms or a $C_1$-$C_4$-halogenoalkoxy having 1 to 5 halogen atoms.

Het represents a heterocycle of the general formula (Het-5)

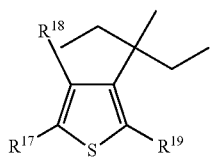
(Het-5)

in which:

R$^{17}$ and R$^{18}$ may be the same or different and may be a hydrogen atom, a halogen atom, a C$_1$-C$_4$-alkyl, a C$_1$-C$_4$-alkyloxy or a C$_1$-C$_4$-halogenoalkyl having 1 to 5 halogen atoms; and R$^{19}$ may be a hydrogen atom, a halogen atom, a C$_1$-C$_4$-alkyl or a C$_1$-C$_4$-halogenoalkyl having 1 to 5 halogen atoms;

provided that the R$^{18}$ and R$^{19}$ are not both a hydrogen atom.

Het represents a heterocycle of the general formula (Het-6)

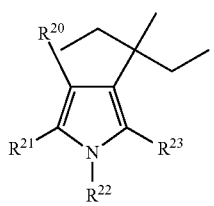
(Het-6)

in which:

R$^{20}$ may be a hydrogen atom, a halogen atom, a cyano group, a C$_1$-C$_4$-alkyl or a C$_1$-C$_4$-halogenoalkyl having 1 to 5 halogen atoms;

R$^{21}$ and R$^{23}$ may be the same or different and may be a hydrogen atom, a halogen atom, a C$_1$-C$_4$-alkyl or a C$_1$-C$_4$-halogenoalkyl having 1 to 5 halogen atoms; and R$^{22}$ may be a hydrogen atom, a cyano group, a C$_1$-C$_4$-alkyl, a C$_1$-C$_4$-halogenoalkyl having 1 to 5 halogen atoms, a C$_1$-C$_4$-alkoxy-C$_1$-C$_4$-alkyl, a hydroxy-C$_1$-C$_4$-alkyl, a C$_1$-C$_4$-alkylsulphonyl, a di(C$_1$-C$_4$-alkyl)aminosulphonyl, a C$_1$-C$_6$-alkylcarbonyl, a phenylsulphonyl optionally substituted by a halogen atom or a C$_1$-C$_4$-alkyl, or a benzoyl optionally substituted by a halogen atom or a C$_1$-C$_4$-alkyl;

provided that the R$^{20}$ and R$^{23}$ are not both a hydrogen atom.

Het represents a heterocycle of the general formula (Het-7)

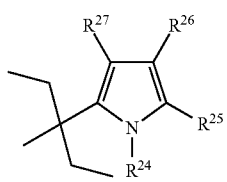
(Het-7)

in which:

R$^{24}$ may be a hydrogen atom, a cyano group, a C$_1$-C$_4$-alkyl, a C$_1$-C$_4$-halogenoalkyl having 1 to 5 halogen atoms, a C$_1$-C$_4$-alkoxy-C$_1$-C$_4$-alkyl, a hydroxy-C$_1$-C$_4$-alkyl, a C$_1$-C$_4$-alkylsulphonyl, a di(C$_1$-C$_4$-alkyl)aminosulphonyl, a C$_1$-C$_6$-alkylcarbonyl, a phenylsulphonyl optionally substituted by a halogen atom or a C$_1$-C$_4$-alkyl, or a benzoyl optionally substituted by a halogen atom or a C$_1$-C$_4$-alkyl; and R$^{25}$, R$^{26}$ and R$^{27}$ may be the same or different and may be a hydrogen atom, a halogen atom, a cyano group, a C$_1$-C$_4$-alkyl, a C$_1$-C$_4$-halogenoalkyl having 1 to 5 halogen atoms or a C$_1$-C$_4$-alkylcarbonyl;

provided that R$^{24}$ and R$^{27}$ are not both a hydrogen atom.

Het represents a heterocycle of the general formula (Het-8)

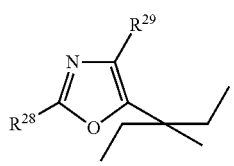
(Het-8)

in which:

R$^{28}$ may be a hydrogen atom or a C$_1$-C$_4$-alkyl; and

R$^{29}$ may be a halogen atom, a C$_1$-C$_4$-alkyl or a C$_1$-C$_4$-halogenoalkyl having 1 to 5 halogen atoms.

Het represents a heterocycle of the general formula (Het-9)

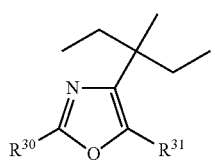
(Het-9)

in which:

R$^{30}$ may be a hydrogen atom or a C$_1$-C$_4$-alkyl; and

R$^{31}$ may be a halogen atom, a C$_1$-C$_4$-alkyl, a C$_1$-C$_4$-halogenoalkyl having 1 to 5 halogen atoms or a phenyl optionally substituted by a halogen atom or a C$_1$-C$_4$-alkyl.

Het represents a heterocycle of the general formula (Het-10)

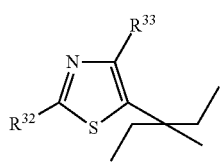
(Het-10)

in which:

R$^{32}$ may be a hydrogen atom, a halogen atom, an amino group, a cyano group, a C$_1$-C$_4$-alkylamino, a di-(C$_1$-C$_4$-alkyl)amino, a C$_1$-C$_4$-alkyl, a C$_1$-C$_4$-halogenoalkyl having 1 to 5 halogen atoms or a phenyl optionally substituted by a halogen atom or a C$_1$-C$_4$-alkyl; and R$^{33}$ may be a halogen atom, a C$_1$-C$_4$-alkyl or a C$_1$-C$_4$-halogenoalkyl having 1 to 5 halogen atoms.

Het represents a heterocycle of the general formula (Het-11)

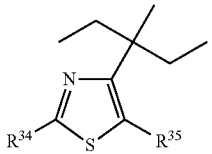
(Het-11)

in which:
R$^{34}$ may be a hydrogen atom, a halogen atom, an amino group, a cyano group, a C$_1$-C$_4$-alkylamino, a di-(C$_1$-C$_4$-alkyl)amino, a C$_1$-C$_4$-alkyl or a C$_1$-C$_4$-halogenoalkyl having 1 to 5 halogen atoms; and
R$^{35}$ may be a halogen atom, a C$_1$-C$_4$-alkyl or a C$_1$-C$_4$-halogenoalkyl having 1 to 5 halogen atoms.

Het represents a heterocycle of the general formula (Het-12)

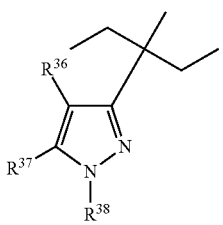
(Het-12)

in which:
R$^{36}$ may be a halogen atom, a cyano group, a nitro group, a C$_1$-C$_4$-alkyl, a C$_1$-C$_4$-halogenoalkyl having 1 to 5 halogen atoms, a C$_3$-C$_6$-cycloalkyl, a C$_1$-C$_4$-alkoxy, a C$_1$-C$_4$-halogenoalkoxy having 1 to 5 halogen atoms, a C$_1$-C$_4$-alkylthio, a C$_1$-C$_4$-halogenoalkylthio having 1 to 5 halogen atoms, an aminocarbonyl group or an aminocarbonyl-C$_1$-C$_4$-alkyl;
R$^{37}$ may be a hydrogen atom, a halogen atom, a cyano group, a nitro group, a C$_1$-C$_4$-alkyl, a C$_1$-C$_4$-alkoxy or a C$_1$-C$_4$-alkylthio; and
R$^{38}$ may be a hydrogen atom, a phenyl, a C$_1$-C$_4$-alkyl, a C$_1$-C$_4$-halogenoalkyl having 1 to 5 halogen atoms, a hydroxy-C$_1$-C$_4$-alkyl, a C$_2$-C$_6$-alkenyl, a C$_3$-C$_6$-cycloalkyl, a C$_1$-C$_4$-alkylthio-C$_1$-C$_4$-alkyl, a C$_1$-C$_4$-halogenoalkylthio-C$_1$-C$_4$-alkyl having 1 to 5 halogen atoms, a C$_1$-C$_4$-alkoxy-C$_1$-C$_4$-alkyl or a C$_1$-C$_4$-halogenoalkoxy-C$_1$-C$_4$-alkyl having 1 to 5 halogen atoms.

Het represents a heterocycle of the general formula (Het-13)

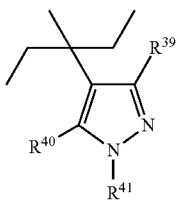
(Het-13)

in which:
R$^{39}$ may be a hydrogen atom, a halogen atom, a cyano group, a nitro group, a C$_1$-C$_4$-alkyl, a C$_1$-C$_4$-halogenoalkyl having 1 to 5 halogen atoms, a C$_3$-C$_6$-cycloalkyl, a C$_1$-C$_4$-alkoxy, a C$_1$-C$_4$-halogenoalkoxy having 1 to 5 halogen atoms, a C$_1$-C$_4$-alkylthio, a C$_1$-C$_4$-halogenoalkylthio having 1 to 5 halogen atoms, an aminocarbonyl or an aminocarbonyl-C$_1$-C$_4$-alkyl;
R$^{40}$ may be a hydrogen atom, a halogen atom, a cyano group, a C$_1$-C$_4$-alkyl, a C$_1$-C$_4$-alkoxy, a C$_1$-C$_4$-halogenoalkoxy having 1 to 5 halogen atoms or a C$_1$-C$_4$-alkylthio; and
R$^{41}$ may be a hydrogen atom, a C$_1$-C$_4$-alkyl, a C$_1$-C$_4$-halogenoalkyl having 1 to 5 halogen atoms, a hydroxy-C$_1$-C$_4$-alkyl, a C$_2$-C$_6$-alkenyl, a C$_3$-C$_6$-cycloalkyl, a C$_1$-C$_4$-alkylthio-C$_1$-C$_4$-alkyl, a C$_1$-C$_4$-halogenoalkylthio-C$_1$-C$_4$-alkyl having 1 to 5 halogen atoms, a C$_1$-C$_4$-alkoxy-C$_1$-C$_4$-alkyl, a C$_1$-C$_4$-halogenoalkoxy-C$_1$-C$_4$-alkyl having 1 to 5 halogen atoms or a phenyl optionally substituted by a halogen atom, a C$_1$-C$_4$-alkyl, a C$_1$-C$_4$-alkoxyalkyl or a nitro group;
provided that the R$^{39}$ and R$^{40}$ are not both a hydrogen atom.

Het represents a heterocycle of the general formula (Het-14)

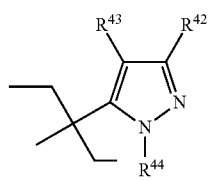
(Het-14)

in which:
R$^{42}$ may be a hydrogen atom, a halogen atom, a cyano group, a nitro group, a C$_1$-C$_4$-alkyl, a C$_1$-C$_4$-halogenoalkyl having 1 to 5 halogen atoms, a C$_3$-C$_6$-cycloalkyl, a C$_1$-C$_4$-alkoxy, a C$_1$-C$_4$-halogenoalkoxy having 1 to 5 halogen atoms, a C$_1$-C$_4$-alkylthio, a C$_1$-C$_4$-halogenoalkylthio having 1 to 5 halogen atoms, an aminocarbonyl, or an aminocarbonyl-C$_1$-C$_4$-alkyl;
R$^{43}$ may be a hydrogen atom, a halogen atom, a cyano group, a C$_1$-C$_4$-alkyl, a C$_1$-C$_4$-alkoxy, a C$_1$-C$_4$-alkylthio or a C$_1$-C$_4$-halogenoalkyl having 1 to 5 halogen atoms;
R$^{44}$ may be a hydrogen atom, a phenyl, a benzyl, a C$_1$-C$_4$-alkyl, a C$_1$-C$_4$-halogenoalkyl having 1 to 5 halogen atoms, a hydroxy-C$_1$-C$_4$-alkyl, a C$_2$-C$_6$-alkenyl, a C$_3$-C$_6$-cycloalkyl, a C$_1$-C$_4$-alkylthio-C$_1$-C$_4$-alkyl, a C$_1$-C$_4$-halogenoalkylthio-C$_1$-C$_4$-alkyl having 1 to 5 halogen atoms, a C$_1$-C$_4$-alkoxy-C$_1$-C$_4$-alkyl, a C$_1$-C$_4$-halogenoalkoxy-C$_1$-C$_4$-alkyl having 1 to 5 halogen atoms;
provided that R$^{43}$ and R$^{44}$ are not both a hydrogen atom.

Het represents a heterocycle of the general formula (Het-15)

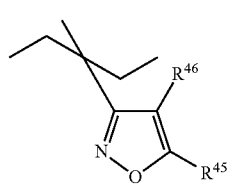
(Het-15)

in which:

$R^{45}$ may be a hydrogen atom, a halogen atom, a $C_1$-$C_4$-alkyl or a $C_1$-$C_4$-halogenoalkyl having 1 to 5 halogen atoms; and $R^{46}$ may be a halogen atom, a $C_1$-$C_4$-alkyl or a $C_1$-$C_4$-halogenoalkyl having 1 to 5 halogen atoms.

Het represents a heterocycle of the general formula (Het-16)

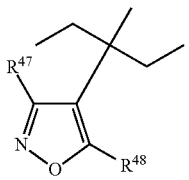

(Het-16)

in which $R^{47}$ and $R^{48}$ may be the same or different and may be a hydrogen atom, a halogen atom, a $C_1$-$C_4$-alkyl, a $C_1$-$C_4$-halogenoalkyl having 1 to 5 halogen atoms, a phenyl optionally substituted by a halogen atom or a $C_1$-$C_4$-alkyl, or a heterocyclyl optionally substituted by a halogen atom or a $C_1$-$C_4$-alkyl;

provided that $R^{47}$ and $R^{48}$ are not both a hydrogen atom.

Het represents a heterocycle of the general formula (Het-17)

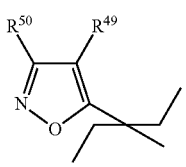

(Het-17)

in which $R^{49}$ may be a halogen atom, a $C_1$-$C_4$-alkyl or a $C_1$-$C_4$-halogenoalkyl having 1 to 5 halogen atoms. and $R^{50}$ may be a halogen atom, a $C_1$-$C_4$-alkyl or a $C_1$-$C_4$-halogenoalkyl having 1 to 5 halogen atoms.

Het represents a heterocycle of the general formula (Het-18)

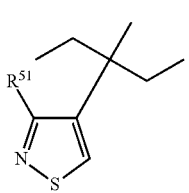

(Het-18)

in which $R^{51}$ may be a halogen atom, a $C_1$-$C_4$-alkyl or a $C_1$-$C_4$-halogenoalkyl having 1 to 5 halogen atoms.

Het represents a heterocycle of the general formula (Het-19)

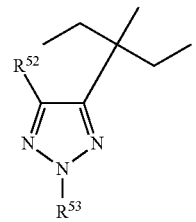

(Het-19)

in which:

$R^{52}$ may be a halogen atom, a $C_1$-$C_4$-alkyl or a $C_1$-$C_4$-halogenoalkyl having 1 to 5 halogen atoms; and $R^{53}$ may be a hydrogen atom, a $C_1$-$C_4$-alkyl, a $C_1$-$C_4$-halogenoalkyl having 1 to 5 halogen atoms, or a phenyl optionally substituted by a halogen atom or a $C_1$-$C_4$-alkyl.

Het represents a heterocycle of the general formula (Het-20)

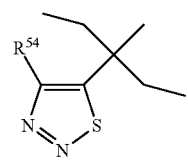

(Het-20)

in which $R^{54}$ may be a halogen atom, a $C_1$-$C_4$-alkyl or a $C_1$-$C_4$-halogenoalkyl having 1 to 5 halogen atoms.

According to the present invention, "Het" of the compound of general formula (I) may be a six membered ring heterocycle. Specific examples of compounds of the present invention where Het is a six membered heterocycle include:

Het represents a heterocycle of the general formula (Het-21)

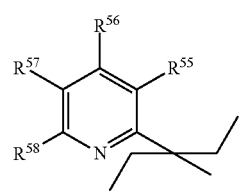

(Het-21)

in which:

$R^{55}$ may be a halogen atom, a hydroxy group, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkylthio having 1 to 5 halogen atoms or a $C_1$-$C_4$-halogenoalkoxy having 1 to 5 halogen atoms;

$R^{56}$, $R^{57}$ and $R^{58}$, which may be the same or different, may be a hydrogen atom, a halogen atom, a cyano group, a $C_1$-$C_4$-alkyl, a $C_1$-$C_4$-halogenoalkyl having 1 to 5 halogen atoms, a $C_1$-$C_4$-alkoxy, a $C_1$-$C_4$-alkylthio, a $C_1$-$C_4$-halogenoalkoxy having 1 to 5 halogen atoms, a $C_1$-$C_4$-alkylsulphinyl or a $C_1$-$C_4$-alkylsulphonyl.

Het represents a heterocycle of the general formula (Het-22)

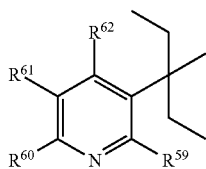
(Het-22)

in which:

R$^{59}$ may be a hydrogen atom, a halogen atom, a hydroxy group, a cyano group, a C$_1$-C$_4$-alkyl, a C$_1$-C$_4$-halogenoalkyl having 1 to 5 halogen atoms, a C$_1$-C$_4$-alkoxy, a C$_1$-C$_5$-alkylthio, a C$_2$-C$_5$-alkenylthio a C$_1$-C$_4$-halogenoalkylthio having 1 to 5 halogen atoms, a C$_1$-C$_4$-halogenoalkoxy having 1 to 5 halogen atoms, a phenyloxy optionally substituted by a halogen atom or a C$_1$-C$_4$-alkyl, or a phenylthio optionally substituted by a halogen atom or a C$_1$-C$_4$-alkyl;

R$^{60}$, R$^{61}$ and R$^{62}$, which may the same or different, may be a hydrogen atom, a halogen atom, a cyano group, a C$_1$-C$_4$-alkyl, a C$_1$-C$_4$-halogenoalkyl having 1 to 5 halogen atoms, a C$_1$-C$_4$-alkoxy, a C$_1$-C$_4$-alkylthio, a C$_1$-C$_4$-halogenoalkoxy having 1 to 5 halogen atoms, a C$_1$-C$_4$-alkylsulphinyl, a C$_1$-C$_4$-alkylsulphonyl or a N-morpholine optionally substituted by a halogen atom or a C$_1$-C$_4$-alkyl, or a thienyl optionally substituted by a halogen atom or a C$_1$-C$_4$-alkyl;

provided that the R$^{59}$ and R$^{62}$ are not both a hydrogen atom.

Het represents a heterocycle of the general formula (Het-23)

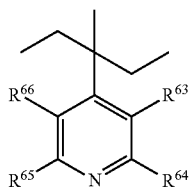
(Het-23)

in which R$^{63}$, R$^{64}$, R$^{65}$ and R$^{66}$, which may be the same or different, may be a hydrogen atom, a halogen atom, a hydroxy group, a cyano group, a C$_1$-C$_4$-alkyl, a C$_1$-C$_4$-halogenoalkyl having 1 to 5 halogen atoms, a C$_1$-C$_4$-alkoxy, a C$_1$-C$_4$-alkylthio, a C$_1$-C$_4$-halogenoalkylthio having 1 to 5 halogen atoms, a C$_1$-C$_4$-halogenoalkoxy having 1 to 5 halogen atoms, a C$_1$-C$_4$-alkylsulphinyl or a C$_1$-C$_4$-alkylsulphonyl;

provided that the R$^{63}$ and R$^{66}$ are not both a hydrogen atom.

Het represents a heterocycle of the general formula (Het-24)

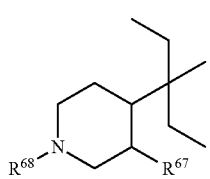
(Het-24)

in which:

R$^{67}$ may be a halogen atom, a C$_1$-C$_4$-alkyl or a C$_1$-C$_4$-halogenoalkyl having 1 to 5 halogen atoms;

R$^{68}$ may be a hydrogen atom, a C$_1$-C$_4$-alkyl, a C$_1$-C$_4$-halogenoalkyl having 1 to 5 halogen atoms, a C$_1$-C$_6$-alkoxycarbonyl, a benzyl optionally substituted by 1 to 3 halogen atoms, a benzyloxycarbonyl optionally substituted by 1 to 3 halogen atoms or a heterocyclyl.

Het represents a heterocycle of the general formula (Het-25)

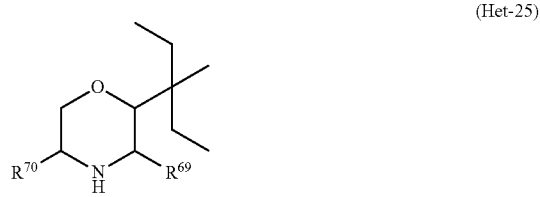
(Het-25)

in which:

R$^{69}$ may be a halogen atom, a hydroxy group, a cyano group, a C$_1$-C$_4$-alkyl, a C$_1$-C$_4$-halogenoalkyl having 1 to 5 halogen atoms, a C$_1$-C$_4$-alkoxy, a C$_1$-C$_4$-alkylthio, a C$_1$-C$_4$-halogenoalkylthio having 1 to 5 halogen atoms or a C$_1$-C$_4$-halogenoalkoxy having 1 to 5 halogen atoms;

R$^{70}$ may be a hydrogen atom, a C$_1$-C$_4$-alkyl, a C$_1$-C$_4$-halogenoalkyl having 1 to 5 halogen atoms or a benzyl.

Het represents a heterocycle of the general formula (Het-26)

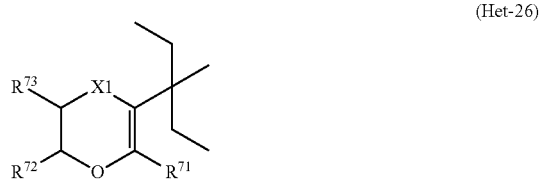
(Het-26)

in which:

X$^1$ may be a sulphur atom, —SO—, —SO$_2$— or —CH$_2$—;

R$^{71}$ may be a C$_1$-C$_4$-alkyl or a C$_1$-C$_4$-halogenoalkyl having 1 to 5 halogen atoms; and R$^{72}$ and R$^{73}$ may be the same or different and may be a hydrogen atom or a Het represents a heterocycle of the general formula (Het-27)

(Het-27)

in which:

R$^{74}$ may be a C$_1$-C$_4$-alkyl or a C$_1$-C$_4$-halogenoalkyl having 1 to 5 halogen atoms;

Het represents a heterocycle of the general formula (Het-28)

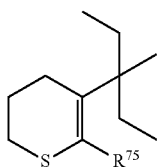
(Het-28)

in which:

$R^{75}$ may be a $C_1$-$C_4$-alkyl or a $C_1$-$C_4$-halogenoalkyl having 1 to 5 halogen atoms.

Het represents a heterocycle of the general formula (Het-29)

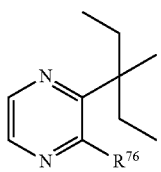
(Het-29)

in which $R^{76}$ may be a halogen atom, a $C_1$-$C_4$-alkyl or a $C_1$-$C_4$-halogenoalkyl having 1 to 5 halogen atoms.

The present invention also relates to a process for the preparation of the compound of general formula (I). Thus, according to a further aspect of the present invention there is provided a process for the preparation of compound of general formula (I) as defined above, which comprises reacting a 2-pyridine derivative of general formula (II) or one of its salt:

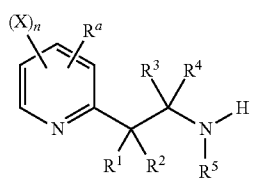
(II)

in which X, n, $R^a$, $R^1$, $R^2$, $R^3$, $R^4$ and $R^5$ are as defined above; with a carboxylic acid derivative of the general formula (III)

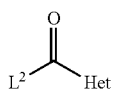
(III)

in which:

Het is as defined above; and $L^2$ is a leaving group chosen as being a halogen atom, a hydroxyl group, —$OR^{77}$, —$OCOR^{77}$, $R^{77}$ being a $C_1$-$C_6$ alkyl, a $C_1$-$C_6$ haloalkyl, a benzyl, 4-methoxybenzyl, pentafluorophenyl or a group of formula

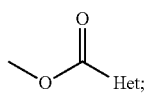

in the presence of a catalyst and, if $L^2$ is a hydroxyl group, in the presence of a condensing agent.

The process according to the present invention is conducted in the presence of a catalyst. Suitable catalyst may be chosen as being 4-dimethyl-aminopyridine, 1-hydroxy-benzotriazole or dimethylformamide.

In case $L^2$ is a hydroxy group, the process according to the present invention is conducted in the presence of condensing agent. Suitable condensing agent may be chosen as being acid halide former, such as phosgene, phosphorous tribromide, phosphorous trichloride, phosphorous pentachloride, phosphorous trichloride oxide or thionyl chloride; anhydride former, such as ethyl chloroformate, methyl chloroformate, isopropyl chloroformate, isobutyl chloroformate or methanesulfonyl-chloride; carbodiimides, such as N,N'-dicyclohexylcarbodiimide (DCC) or other customary condensing agents, such as phosphorous pentoxide, polyphosphoric acid, N,N'-carbonyl-diimidazole, 2-ethoxy-N-ethoxycarbonyl-1,2-dihydroquinoline (EEDQ), triphenylphosphine/tetrachloromethane, 4-(4,6-dimethoxy[1.3.5]triazin-2-yl)-4-methylmorpholinium chloride hydrate or bromotripyrrolidino-phosphonium-hexafluorophosphate.

When $R^5$ is a hydrogen atom, the above mentioned process for the preparation of compound of general formula (I) may optionally be completed by a further step according to the following reaction scheme:

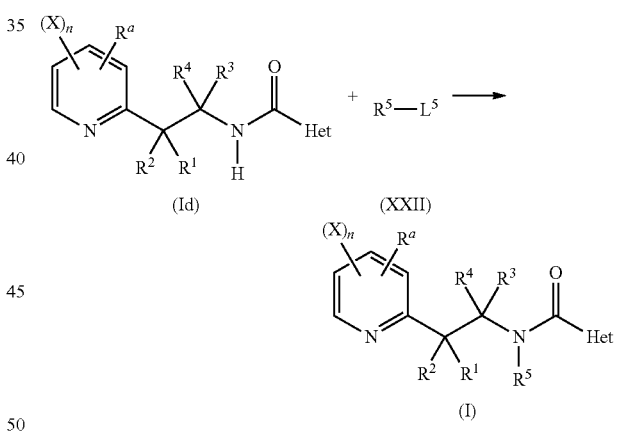

in which: —$R^1$, $R^2$, $R^3$, $R^4$, $R^5$, $R^a$, X, n and Het are as defined above;

$L^5$ is a leaving group chosen as being a halogen atom, a 4-methyl phenylsulfonyloxy or a methylsulfonyloxy;
comprising the reaction of a compound of general formula (Id) with a compound of general formula (XXII) to provide a compound of general formula (I).

Depending on the definition of $R^1$, $R^2$, $R^3$, $R^4$ or $R^5$, amine derivatives of general formula (II) may be prepared by different processes. One example (A) of such a process may be when:

$R^a$, $R^2$, X, n are as defined above;

$R^1$ is a hydrogen atom or a $C_1$-$C_6$ alkyl; and $R^3$, $R^4$, $R^5$ are hydrogen atoms;

then, the amine derivative of general formula (II) may be prepared according to a process which comprises:

a first step according to reaction scheme A-1:

Scheme A-1

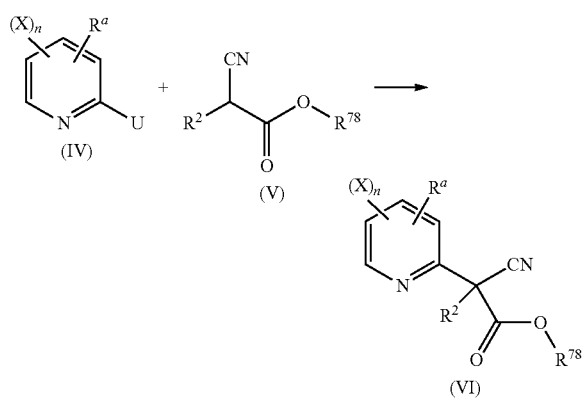

in which: —$R^a$, $R^2$, X and n are as defined above;
$R^{78}$ is a $C_1$-$C_6$ alkyl, a $C_1$-$C_6$ haloalkyl, a benzyl, 4-methoxybenzyl or pentafluorophenyl;
U is a leaving group chosen as being a halogen, a $C_1$-$C_6$ alkylsulfonate or a $C_1$-$C_6$ haloalkylsulfonate;
comprising the acylation of a cyanoacetate derivative of general formula (V) by a pyridine derivative of general formula (IV), to provide a 2-(pyridyl)cyanoacetate derivative of general formula (VI), in the presence of a base, at a temperature of from 0° C. to 200° C.;

a second step according to reaction scheme A-2:

Scheme A-2

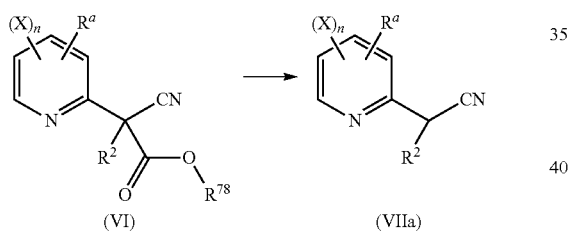

in which: —$R^a$, $R^2$, X, n are as defined above;
$R^{78}$ is a $C_1$-$C_6$ alkyl, a $C_1$-$C_6$ haloalkyl, a benzyl, 4-methoxybenzyl or pentafluorophenyl;
comprising a basic hydrolysis, an acidic hydrolysis or a displacement by an halide of a compound of general formula (VI) in the same or a different pot to provide, upon heating at a temperature of from 40° C. to reflux, a 2-pyridylacetonitrile derivative of general formula (VIIa);

a third step according to reaction scheme A-3:

Scheme A-3

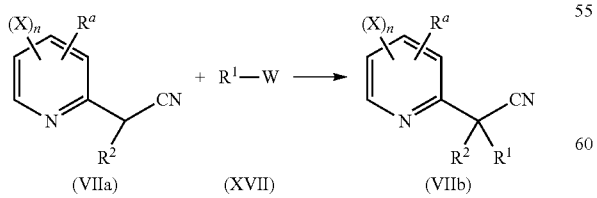

in which: —$R^a$, $R^2$, X, n are as defined above;
$R^1$ is a $C_1$-$C_6$ alkyl;
W is a halogen atom, a $C_1$-$C_6$ alkylsulfonate, a $C_1$-$C_6$ haloalkylsulfonate or a 4-methyl-phenylsulfonate;

comprising the alkylation of a compound of general formula (VIIa) by a reagent of general formula (XVII) to provide a compound of general formula (VIIb);

a fourth step according to reaction scheme A-4:

Scheme A-4

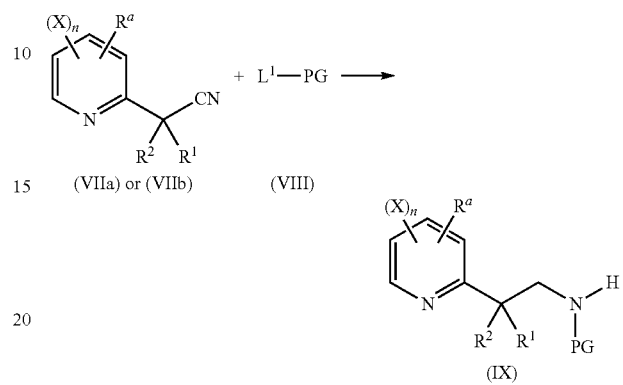

in which: —$R^a$, $R^2$, X, n are as defined above;
$R^1$ is a hydrogen atom or a $C_1$-$C_6$ alkyl;
$L^1$ is a leaving group chosen as being a —$OR^{77}$ group or a —$OCOR^{77}$ group, $R^{77}$ being a $C_1$-$C_6$ alkyl, a $C_1$-$C_6$ haloalkyl, a benzyl, 4-methoxybenzyl or pentafluorophenyl;
PG represents a protecting group which may be a —$COOR^{77}$ group or —$COR^{77}$ group, $R^{77}$ being a $C_1$-$C_6$ alkyl, a $C_1$-$C_6$ haloalkyl, a benzyl, 4-methoxybenzyl or pentafluorophenyl;

comprising the reduction, by hydrogenation or by an hydride donor, of a compound of general formula (VIIa) or (VIIb), in the presence of a catalyst and in the presence of a compound of general formula (VIII) to produce a compound of general formula (IX), at a temperature of from 0° C. to 150° C. and under a pressure of from 1 bar and 100 bar;

a fifth step according to reaction scheme A-5:

Scheme A-5

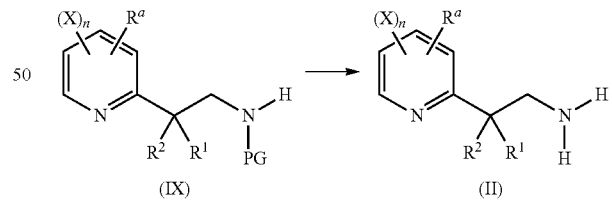

in which: —$R^a$, $R^2$, X, n are as defined above;
$R^1$ is a hydrogen atom or a $C_1$-$C_6$ alkyl;
PG represents a protecting group which may be a —$COOR^{77}$ group or —$COR^{77}$ group, $R^{77}$ being a $C_1$-$C_6$ alkyl, a $C_1$-$C_6$ haloalkyl, a benzyl, 4-methoxybenzyl or pentafluorophenyl;

comprising a deprotection reaction, in an acidic or in a basic medium, of a compound of general formula (IX) to provide an amine derivative of general formula (II) or one of its salt.

The first step (step A-1) is conducted in the presence of a base. Preferably, the base will be chosen as being an inorganic or an organic base. Suitable examples of such bases may for example be alkaline earth metal or alkali metal hydrides, hydroxides, amides, alcoholates, carbonates or hydrogen carbonates, acetates or tertiary amines.

The first step (step A-1) according to the present invention is conducted at a temperature of from 0° C. to 200° C. Preferably, first step (step A-1) is conducted at a temperature of from 0° C. to 120° C., more preferably at a temperature of from 0° C. to 80° C.

The first step (step A-1) according to the present invention may be conducted in the presence of a solvent. Preferably, the solvent is chosen as being water, an organic solvent or a mixture of both. Suitable organic solvents may for example be aliphatic, alicyclic or aromatic solvent.

The first step (step A-1) according to the present invention may also be conducted in the presence of a catalyst. Preferably, the catalyst is chosen as being palladium salts or complexes. More preferably, the catalyst is chosen as being a palladium complex. Suitable palladium complex catalyst may for example be generated directly in the reaction mixture by separately adding to the reaction mixture a palladium salt and a complex ligand. Suitable ligands may for example be bulky phosphines or arsines ligands, such as (R)-(–)-1-[(S)-2-(dicyclohexylphosphino)ferrocenyl]ethyldicyclohexylphosphine and its corresponding enantiomer, or a mixture of both; (R)-(–)-1[(S)-2-(dicyclohexylphosphino)ferrocenyl]ethyldiphenylphosphine and its corresponding enantiomer, or a mixture of both; (R)-(–)-1[(S)-2-(diphenylphosphino)ferrocenyl]ethyldi-t-butylphosphine and its corresponding enantiomer, or a mixture of both; or (R)-(–)-1[(S)-2-(diphenylphosphino)ferrocenyl]ethyldicyclohexylphosphine and its corresponding enantiomer, or a mixture of both.

The fourth step (step A-4) according to the present invention is conducted in the presence of a hydride donor. Preferably, the hydride donor is chosen as being metal or metalloid hydrides such as $LiAlH_4$, $NaBH_4$, $KBH_4$, $B_2H_6$.

The fourth step (step A-4) according to the present invention is conducted in the presence of a catalyst. Preferably, the catalyst is chosen as being Co(II)-Chloride, Ni(II)-chloride, ammonia or one of its salt, Palladium on charcoal, Raney Nickel, Raney Cobalt or Platinum.

The fourth step (step A-4) according to the present invention is conducted at a temperature of from 0° C. to 150° C. Preferably the temperature is of from 10° C. to 120° C. More preferably, the temperature is of from 10° C. to 80° C.

The fourth step (step A-4) according to the present invention is conducted under a pressure of from 1 bar to 100 bar. Preferably the pressure is of from 1 bar to 50 bar.

The fourth step (step A-4) according to the present invention may be conducted in the presence of an organic solvent, of water or of a mixture thereof. Preferably, the solvent is chosen as being ether, alcohol, carboxylic acid, or a mixture thereof with water or pure water.

A second example (B) of such a process may be when:
$R^a$, $R^1$, $R^2$, X, n are as defined above; and
$R^3$, $R^4$, $R^5$ are hydrogen atoms;
then, the amine derivative of general formula (II) may be prepared according to a process which comprises:

a first step according to reaction scheme B-1:

Scheme B-1

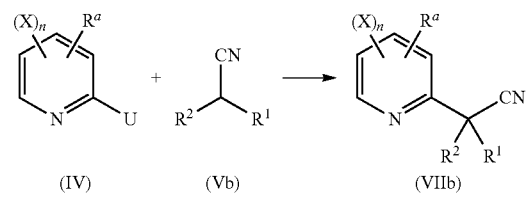

(IV)    (Vb)    (VIIb)

in which: —$R^a$, $R^1$, $R^2$, X and n are as defined above;
U is a leaving group chosen as being a halogen atom, a $C_1$-$C_6$ alkylsulfonate or a $C_1$-$C_6$ haloalkylsulfonate;
comprising the arylation of a compound of general formula (Vb) by a pyridine derivative of general formula (IV) to provide a 2-pyridylacetonitrile derivative of general formula (VIIb), in the presence of a base and at a at temperature of from –100° C. to 200° C.;

a second step according to reaction scheme B-2:

Scheme B-2

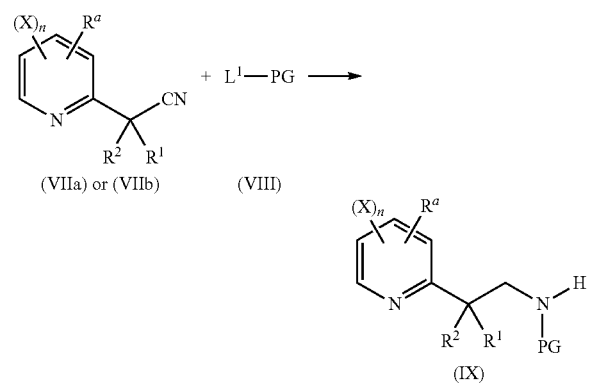

(VIIa) or (VIIb)    (VIII)

(IX)

in which: —$R^a$, $R^1$, $R^2$, X and n are as defined above;
$L^1$ is a leaving group chosen as being a —$OR^{79}$ group or a —$OCOR^{79}$ group, $R^{79}$ being a $C_1$-$C_6$ alkyl, a $C_1$-$C_6$ haloalkyl, a benzyl, 4-methoxybenzyl or pentafluorophenyl;
PG represents a protecting group which may be a —$COOR^{79}$ group or —$COR^{79}$ group, $R^{79}$ being a $C_1$-$C_6$ alkyl, a $C_1$-$C_6$ haloalkyl, a benzyl, 4-methoxybenzyl or pentafluorophenyl;
comprising the reduction, by hydrogenation or by an hydride donor, of a compound of general formula (VIIa) or (VIIb), in the presence of a compound of general formula (VIII) to produce a compound of general formula (IX);

a third step according to reaction scheme B-3:

Scheme B-3

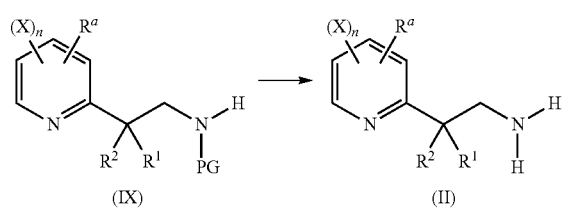

(IX)    (II)

in which: —$R^a$, $R^1$, $R^2$, X and n are as defined above;

PG represents a protecting group which may be a —$COOR^{79}$ group or —$COR^{79}$ group, $R^{79}$ being a $C_1$-$C_6$ alkyl, a $C_1$-$C_6$ haloalkyl, a benzyl, 4-methoxybenzyl or pentafluorophenyl;

comprising a deprotection reaction, in an acidic or in a basic medium, of a compound of general formula (IX) to provide an amine derivative of general formula (II) or one of its salt.

The first step (step B-1) is conducted at a temperature of from −100° C. to 200° C. Preferably, first step (step A-1) is conducted at a temperature of from −80° C. to 120° C., more preferably at a temperature of from −80° C. to 80° C.

The first step (step B-1) according to the present invention is conducted in the presence of a base. Preferably, the base will be chosen as being an inorganic or an organic base. Suitable examples of such bases may for example be alkaline earth metal or alkali metal hydrides, hydroxides, amides, alcoholates, carbonates or hydrogen carbonates, acetates or tertiary amines.

The first step (step B-1) according to the present invention may be conducted in the presence of a solvent. Preferably, the solvent is chosen as being water, an organic solvent or a mixture of both. Suitable organic solvents may for example be aliphatic, alicyclic or aromatic solvent.

The first step (step B-1) according to the present invention may also be conducted in the presence of a catalyst. Preferably, the catalyst is chosen as being palladium salts or complexes. More preferably, the catalyst is chosen as being a palladium complex. Suitable palladium complex catalyst may for example be generated directly in the reaction mixture by separately adding to the reaction mixture a palladium salt and a complex ligand. Suitable ligands may for example be bulky phosphines or arsines ligands, such as (R)-(−)-1-[(S)-2-(dicyclohexylphosphino)ferrocenyl]ethyldicyclohexylphosphine and its corresponding enantiomer, or a mixture of both; (R)-(−)-1[(S)-2-(dicyclohexylphosphino)ferrocenyl]ethyldiphenylphosphine and its corresponding enantiomer, or a mixture of both; (R)-(−)-1[(S)-2-(diphenylphosphino)ferrocenyl]ethyldi-t-butylphosphine and its corresponding enantiomer, or a mixture of both; or (R)-(−)-1[(S)-2-(diphenylphosphino)ferrocenyl]ethyldicyclohexylphosphine and its corresponding enantiomer, or a mixture of both.

The preferred conditions under which step B-2 is conducted are the same than the preferred conditions under which step A-4 of the above mentioned process A is conducted.

The preferred conditions under which step B-3 is conducted are the same than the preferred conditions under which step A-5 of the above mentioned process A is conducted.

A third example (C) of such a process may be when:

$R^a$, $R^2$, X, n are as defined above;

$R^1$ is a formylamino, a $C_1$-$C_8$-alkylcarbonylamino, a $C_1$-$C_8$-halogenoalkylcarbonylamino having 1 to 5 halogen atoms, a phenylcarbonylamino or a 2,6-dichlorophenylcarbonylamino; and $R^3$, $R^4$, $R^5$ are hydrogen atoms;

then, the amine derivative of general formula (II) may be prepared according to a process comprising:

a first step according to reaction scheme C-1:

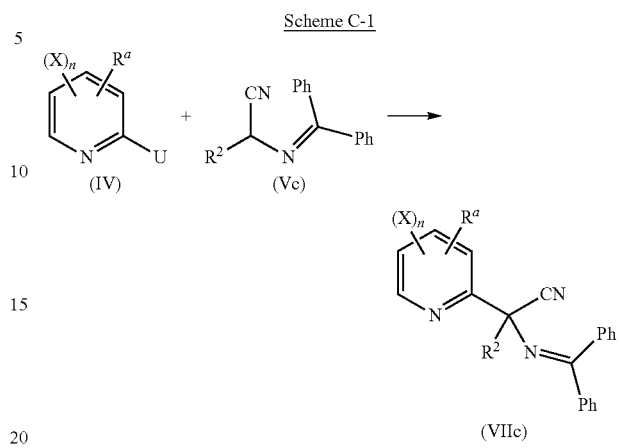

in which: —$R^a$, $R^2$, X, n are as defined above;

U is a leaving group chosen as being a halogen atom, a $C_1$-$C_6$ alkylsulfonate or a $C_1$-$C_6$ haloalkylsulfonate;

comprising the arylation of a compound of general formula (Vc) by a pyridine derivative of general formula (IV) to provide a 2-pyridylacetonitrile derivative of general formula (VIIc), in the presence of a base and at a at temperature of from −100° C. to 200° C.;

a second step according to reaction scheme C-2:

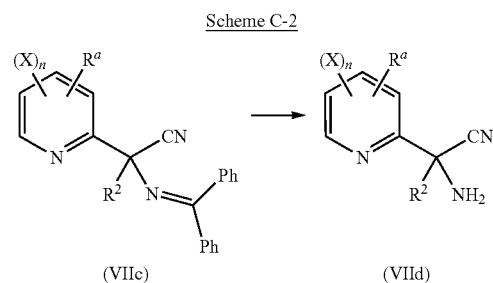

in which $R^a$, $R^2$, X, n are as defined above;

comprising the de-protection, by acidic hydrolysis, of a compound of general formula (VIIc), to produce a compound of general formula (VIId) or one of its salt;

a third step according to reaction scheme C-3:

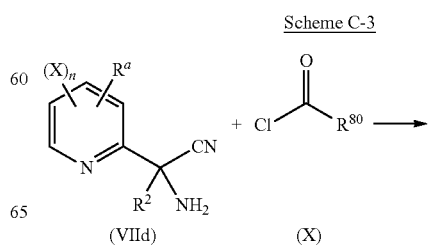

-continued

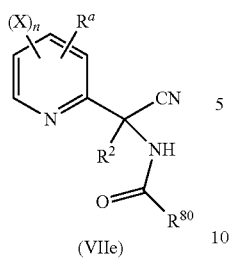

(VIIe)

in which: —$R^a$, $R^2$, X, n are as defined above;
$R^{80}$ is a hydrogen atom, a $C_1$-$C_6$ alkyl group, a $C_1$-$C_8$-halogenoalkyl having 1 to 5 halogen atoms, a phenyl or 2,6 dichlorophenyl;
comprising the coupling between a compound of general formula (VIId) and an acyl chloride of general formula (X) to produce a compound of general formula (VIIe).

a fourth step according to reaction scheme C-4:

Scheme C-4

(VIIe)  (VIII)

(IXb)

in which: —$R^a$, $R^2$, X, n are as defined above;
$R^{80}$ is a hydrogen atom, a $C_1$-$C_6$ alkyl group, a $C_1$-$C_8$-halogenoalkyl having 1 to 5 halogen atoms, a phenyl or 2,6 dichlorophenyl;
$L^1$ is a leaving group chosen as being a —$OR^{79}$ group or a $OCOR^{79}$ group, $R^{79}$ being a $C_1$-$C_6$ alkyl, a $C_1$-$C_6$ haloalkyl, a benzyl, 4-methoxybenzyl or pentafluorophenyl;
PG represents a protecting group which may be a —$COOR^{79}$ group or —$COR^{79}$ group, $R^{79}$ being a $C_1$-$C_6$ alkyl, a $C_1$-$C_6$ haloalkyl, a benzyl, 4-methoxybenzyl or pentafluorophenyl;
comprising the reduction, by hydrogenation or by an hydride donor, of a compound of general formula (VIIe), in the presence of a compound of general formula (VIII) to produce a compound of general formula (IXb);

a fifth step according to scheme C-5

Scheme C-5

(IXb) → (II)

in which: —$R^a$, $R^2$, X, n are as defined above;
$R^{80}$ is a hydrogen atom, a $C_1$-$C_6$ alkyl group, a $C_1$-$C_8$-halogenoalkyl having 1 to 5 halogen atoms, a phenyl or 2,6 dichlorophenyl;
$L^1$ is a leaving group chosen as being a —$OR^{79}$ group or a $OCOR^{79}$ group, $R^{79}$ being a $C_1$-$C_6$ alkyl, a $C_1$-$C_6$ haloalkyl, a benzyl, 4-methoxybenzyl or pentafluorophenyl;
PG represents a protecting group which may be a —$COOR^{79}$ group or —$COR^{79}$ group, $R^{79}$ being a $C_1$-$C_6$ alkyl, a $C_1$-$C_6$ haloalkyl, a benzyl, 4-methoxybenzyl or pentafluorophenyl;
comprising a deprotection reaction, in an acidic or in a basic medium, of a compound of general formula (IXb) to provide an amine derivative of general formula (II) or one of its salt.

A fourth example (D) of such a process may be when:
$R^a$, $R^b$, $R^1$, X, Y, n and p are as defined above;
$R^2$ is a hydrogen atom;
$R^3$ is a $C_1$-$C_6$ alkyl, a $C_1$-$C_6$ haloalkyl, a benzyl or a phenyl; and
$R^5$ is a hydrogen atom, a $C_1$-$C_6$ alkyl, a $C_1$-$C_6$ haloalkyl, a $C_1$-$C_6$ alkoxy or a $C_3$-$C_7$ cycloalkyl;
then, the amine derivative of general formula (II) may be prepared according to a process comprising:

a first step according to reaction scheme D-1:

Scheme D-1

(IV) + (XI) → (XII)

in which: —$R^a$, $R^1$, X and n are as defined above;
$R^3$ is a $C_1$-$C_6$ alkyl, a $C_1$-$C_6$ haloalkyl, a benzyl or a phenyl:
$R^{78}$ is a $C_1$-$C_6$ alkyl, a $C_1$-$C_6$ haloalkyl, a benzyl, 4-methoxybenzyl or pentafluorophenyl;
U is a leaving group chosen as being a halogen, a $C_1$-$C_6$ alkylsulfonate or a $C_1$-$C_6$ haloalkylsulfonate;

comprising the arylation of a ketoacetate derivative of general formula (XI) by a pyridine derivative of general formula (IV), to provide a 2-(pyridyl)ketoacetate derivative of general formula (XII), in the presence of a base, at a temperature of from 0° C. to 200° C.;

a second step according to reaction scheme D-2:

Scheme D-2

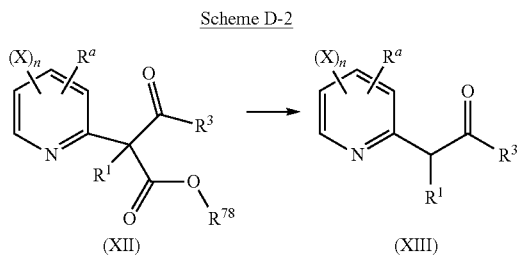

(XII)           (XIII)

in which: —$R^a$, $R^1$, X, n are as defined above;
$R^2$ is a hydrogen atom;
$R^3$ is a $C_1$-$C_6$ alkyl, a $C_1$-$C_6$ haloalkyl, a benzyl or a phenyl;
$R^{78}$ is a $C_1$-$C_6$ alkyl, a $C_1$-$C_6$ haloalkyl, a benzyl, 4-methoxybenzyl or pentafluorophenyl;
comprising a basic hydrolysis, an acidic hydrolysis or a displacement by an halide of a compound of general formula (XII) in the same or a different pot to provide, upon heating at a temperature of from 40° C. to reflux, a 2-pyridylketone derivative of general formula (XIII);

a third step according to reaction scheme D-3:

Scheme D-3

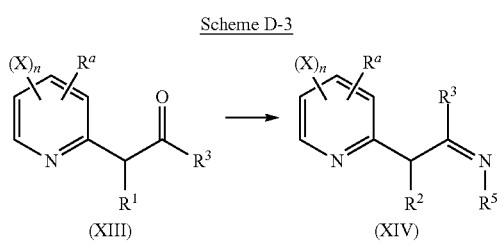

(XIII)           (XIV)

in which: —$R^a$, $R^1$, X and n are as defined above;
$R^2$ is a hydrogen atom;
$R^3$ is a $C_1$-$C_6$ alkyl, a $C_1$-$C_6$ haloalkyl, a benzyl or a phenyl;
$R^5$ is a hydrogen atom, a $C_1$-$C_6$ alkyl, a $C_1$-$C_6$ haloalkyl, a $C_1$-$C_6$ alkoxy or a $C_3$-$C_7$ cycloalkyl;
comprising the reaction of a compound of general formula (XIII) with an amine of formula $R^5$—NH2 to provide an imine derivative of general formula (XIV);

a fourth step according to scheme D-4:

Scheme D-4

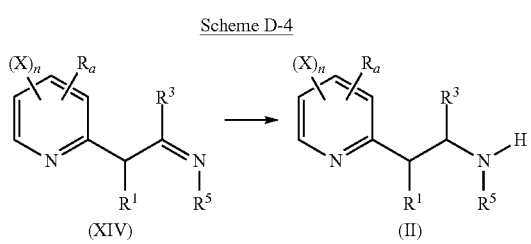

(XIV)           (II)

in which: —$R^a$, $R^1$, X and n are as defined above;
$R^2$ is a hydrogen atom;
$R^3$ is a $C_1$-$C_6$ alkyl, a $C_1$-$C_6$ haloalkyl, a benzyl, a phenyl;

$R^5$ is a hydrogen atom, a $C_1$-$C_6$ alkyl, a $C_1$-$C_6$ haloalkyl, a $C_1$-$C_6$ alkoxy or a $C_3$-$C_7$ cycloalkyl;
comprising the reduction of an imine derivative of general formula (XIV) by hydrogenation or by an hydride donor, in the same or a different pot to provide an amine derivative of general formula (II) or one of its salt.

A fifth example (E) of such a process may be when:
$R^a$, $R^b$, $R^1$, $R^2$, X, Y, n and p are as defined above;
$R^3$ is a hydrogen atom
$R^4$ is a $C_1$-$C_6$ alkyl, a $C_1$-$C_6$ haloalkyl, a benzyl, a phenyl; and
$R^5$ is a hydrogen atom, a $C_1$-$C_6$ alkyl, a $C_1$-$C_6$ haloalkyl, a $C_1$-$C_6$ alkoxy or a $C_3$-$C_7$ cycloalkyl;
then, the amine derivative of general formula (II) may be prepared according to a process comprising:

a first step according to reaction scheme E-1:

Scheme E-1

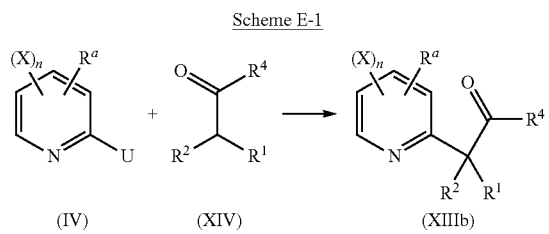

(IV)      (XIV)      (XIIIb)

in which: —$R^a$, $R^1$, $R^2$, X and n are as defined above;
$R^4$ is a $C_1$-$C_6$ alkyl, a $C_1$-$C_6$ haloalkyl, a benzyl or a phenyl:
U is a leaving group chosen as being a halogen, a $C_1$-$C_6$ alkylsulfonate or a $C_1$-$C_6$ haloalkylsulfonate;
comprising the arylation of a ketone derivative of general formula (XIV) by a pyridine derivative of general formula (IV), to provide a 2-(pyridyl)ketone derivative of general formula (XIIIb), in the presence of a base, at a temperature of from 0° C. to 200° C.;

a second step according to reaction scheme E-2:

Scheme E-2

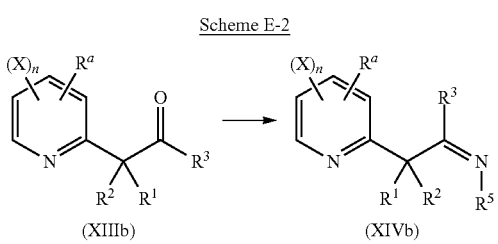

(XIIIb)           (XIVb)

in which: —$R^a$, $R^1$, $R^2$, X and n are as defined above;
$R^4$ is a $C_1$-$C_6$ alkyl, a $C_1$-$C_6$ haloalkyl, a benzyl or a phenyl:
$R^5$ is a hydrogen atom, a $C_1$-$C_6$ alkyl, a $C_1$-$C_6$ haloalkyl, a $C_1$-$C_6$ alkoxy or a $C_3$-$C_7$ cycloalkyl;
comprising the reaction of a compound of general formula (XIIIb) with an amine of formula $R^5$—NH2 to provide an imine derivative of general formula (XIVb);

a third step according to scheme E-3:

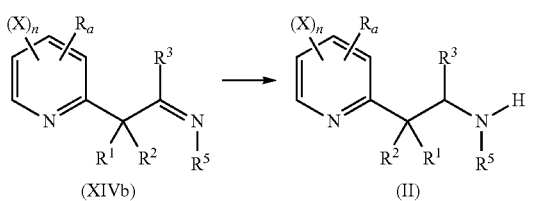

in which: —$R^a$, $R^1$, $R^2$, X and n are as defined above;
$R^3$ is a $C_1$-$C_6$ alkyl, a $C_1$-$C_6$ haloalkyl, a benzyl or a phenyl;
$R^4$ is a hydrogen atom;
$R^5$ is a hydrogen atom, a $C_1$-$C_6$ alkyl, a $C_1$-$C_6$ haloalkyl, a $C_1$-$C_6$ alkoxy or a $C_3$-$C_7$ cycloalkyl;
  comprising the reduction of an imine derivative of general formula (XIVb) by hydrogenation or by an hydride donor, in the same or a different pot to provide an amine derivative of general formula (II) or one of its salt.

A sixth example (F) of such a process may be when:
$R^a$, $R^2$, X, n are as defined above;
$R^1$ is a cyano group, a hydroxy group, a $C_2$-$C_6$-alkynyl, a $C_1$-$C_6$-alkylamino, a di-$C_1$-$C_6$-alkylamino, a $C_1$-$C_6$-alkoxy, a $C_1$-$C_6$-halogenoalkoxy having 1 to 5 halogen atoms, a $C_1$-$C_6$-alkylsulfanyl, a $C_1$-$C_6$-halogenoalkylsulfanyl having 1 to 5 halogen atoms, a $C_2$-$C_6$-alkenyloxy, a $C_2$-$C_6$-halogenoalkenyloxy having 1 to 5 halogen atoms, a $C_3$-$C_6$-alkynyloxy, a $C_3$-$C_6$-halogenoalkynyloxy having 1 to 5 halogen atoms, a benzyloxy, a benzylsulfanyl, a benzylamino, a phenoxy, a phenylsulfanyl, a phenylamino, or a phenyl sulphanyl group, a $C_1$-$C_6$-alkylcarbonyloxy, a $C_1$-$C_6$-halogenoalkylcarbonyloxy having 1 to 5 halogen atoms; and
$R^3$ and $R^4$ are hydrogen atoms;
  then, the amine derivative of general formula (II) may be prepared according to a process comprising:
a first step according to reaction scheme F-1:

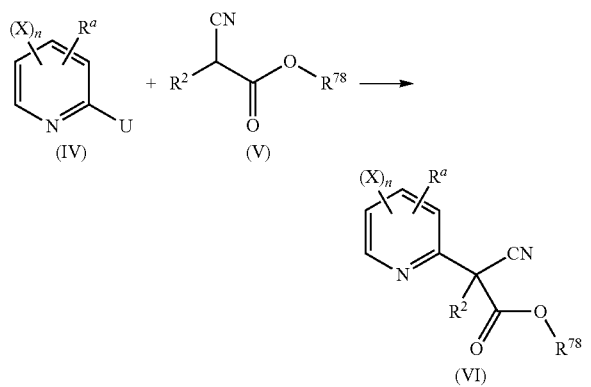

in which: —$R^a$, $R^2$, X and n are as defined above;
$R^{78}$ is a $C_1$-$C_6$ alkyl, a $C_1$-$C_6$ haloalkyl, a benzyl, 4-methoxybenzyl or pentafluorophenyl;
U is a leaving group chosen as being a halogen, a $C_1$-$C_6$ alkylsulfonate or a $C_1$-$C_6$ haloalkylsulfonate;

comprising the arylation of a cyanoacetate derivative of general formula (V) by a pyridine derivative of general formula (IV), to provide a 2-(pyridyl)cyanoacetate derivative of general formula (VI), in the presence of a base, at a temperature of from 0° C. to 200° C.;
a second step according to reaction scheme F-2:

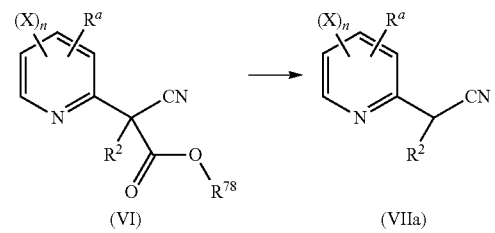

in which: —$R^a$, $R^2$, X, n are as defined above;
$R^1$ is a hydrogen atom;
$R^{78}$ is a $C_1$-$C_6$ alkyl, a $C_1$-$C_6$ haloalkyl, a benzyl, 4-methoxybenzyl or pentafluorophenyl;
comprising a basic hydrolysis, an acidic hydrolysis or a displacement by an halide of a compound of general formula (VI) in the same or a different pot to provide, upon heating at a temperature of from 40° C. to reflux, a 2-pyridylacetonitrile derivative of general formula (VIIa);
a third step according to reaction scheme F-3:

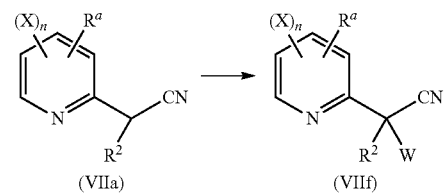

in which: —$R^a$, $R^2$, X, n are as defined above;
W is a halogen atom;
  comprising the halogenation of a compound of general formula (VIIa) to provide a compound of general formula (VIII);
a fourth step according to reaction scheme F-4:

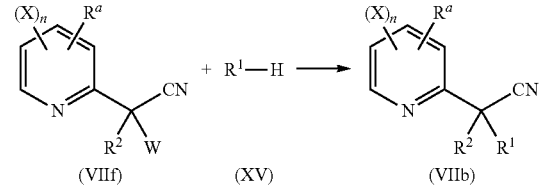

in which: —$R^a$, $R^2$, X, n are as defined above;
W is a halogen atom;
$R^1$ is a cyano group, a hydroxy group, a $C_2$-$C_6$-alkynyl, a $C_1$-$C_6$-alkylamino, a di-$C_1$-$C_6$-alkylamino, a $C_1$-$C_6$-alkoxy, a $C_1$-$C_6$-halogenoalkoxy having 1 to 5 halogen atoms, a $C_1$-$C_6$-alkylsulfanyl, a $C_1$-$C_6$-halogenoalkylsulfanyl having 1 to 5 halogen atoms, a $C_2$-$C_6$-alkenyloxy, a $C_2$-$C_6$-halogenoalkenyloxy having 1 to 5 halogen atoms, a $C_3$-$C_6$-alkynyloxy, a $C_3$-$C_6$-halogenoalkynyloxy having 1 to 5 halogen atoms, a benzyloxy, a benzylsulfanyl, a benzylamino, a phenoxy, a phenylsulfanyl, a phenylamino, or a phenyl sulphanyl group, a $C_1$-$C_6$-alkylcarbonyloxy or a $C_1$-$C_6$-halogenoalkylcarbonyloxy having 1 to 5 halogen atoms;

comprising the nucleophilic substitution, in the presence of a base, of a compound of general formula (VIII) in the presence of a compound of general formula (XV) to produce a compound of general formula (VIIb), at a temperature of from −78° C. to 150° C., a fifth step according to reaction scheme F-5:

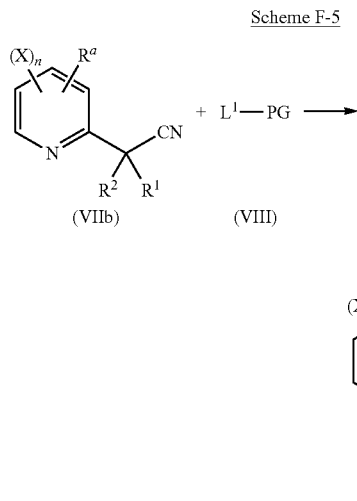

Scheme F-5

(VIIb)  (VIII)

(IX)

in which: —$R^a$, $R^2$, X, n are as defined above;

$R^1$ is a cyano group, a hydroxy group, a $C_2$-$C_6$-alkynyl, a $C_1$-$C_6$-alkylamino, a di-$C_1$-$C_6$-alkylamino, a $C_1$-$C_6$-alkoxy, a $C_1$-$C_6$-halogenoalkoxy having 1 to 5 halogen atoms, a $C_1$-$C_6$-alkylsulfanyl, a $C_1$-$C_6$-halogenoalkylsulfanyl having 1 to 5 halogen atoms, a $C_2$-$C_6$-alkenyloxy, a $C_2$-$C_6$-halogenoalkenyloxy having 1 to 5 halogen atoms, a $C_3$-$C_6$-alkynyloxy, a $C_3$-$C_6$-halogenoalkynyloxy having 1 to 5 halogen atoms, a benzyloxy, a benzylsulfanyl, a benzylamino, a phenoxy, a phenylsulfanyl, a phenylamino, or a phenyl sulphanyl group, a $C_1$-$C_6$-alkylcarbonyloxy or a $C_1$-$C_6$-halogenoalkylcarbonyloxy having 1 to 5 halogen atoms;

$L^1$ is a leaving group chosen as being a —$OR^{79}$ group or a —$OCOR^{79}$ group, $R^{79}$ being a $C_1$-$C_6$ alkyl, a $C_1$-$C_6$ haloalkyl, a benzyl, 4-methoxybenzyl or pentafluorophenyl;

PG represents a protecting group which may be a —$COOR^{79}$ group or —$COR^{79}$ group, $R^{79}$ being a $C_1$-$C_6$ alkyl, a $C_1$-$C_6$ haloalkyl, a benzyl, 4-methoxybenzyl or pentafluorophenyl;

comprising the reduction, by hydrogenation or by an hydride donor, of a compound of general formula (VIIb), in the presence of a catalyst and in the presence of a compound of general formula (VIII) to produce a compound of general formula (IX), at a temperature of from 0° C. to 150° C. and under a pressure of from 1 bar and 100 bar;

a sixth step according to reaction scheme F-6:

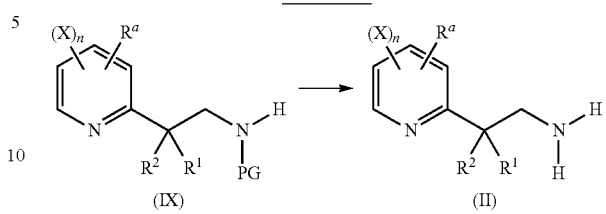

Scheme F-6

(IX)  (II)

in which: —$R^a$, $R^2$, X, n are as defined above;

$R^1$ is a cyano group, a hydroxy group, a $C_2$-$C_6$-alkynyl, a $C_1$-$C_6$-alkylamino, a di-$C_1$-$C_6$-alkylamino, a $C_1$-$C_6$-alkoxy, a $C_1$-$C_6$-halogenoalkoxy having 1 to 5 halogen atoms, a $C_1$-$C_6$-alkylsulfanyl, a $C_1$-$C_6$-halogenoalkylsulfanyl having 1 to 5 halogen atoms, a $C_2$-$C_6$-alkenyloxy, a $C_2$-$C_6$-halogenoalkenyloxy having 1 to 5 halogen atoms, a $C_3$-$C_6$-alkynyloxy, a $C_3$-$C_6$-halogenoalkynyloxy having 1 to 5 halogen atoms, a benzyloxy, a benzylsulfanyl, a benzylamino, a phenoxy, a phenylsulfanyl, a phenylamino, or a phenyl sulphanyl group, a $C_1$-$C_6$-alkylcarbonyloxy or a $C_1$-$C_6$-halogenoalkylcarbonyloxy having 1 to 5 halogen atoms;

PG represents a protecting group which may be a —$COOR^{79}$ group or —$COR^{79}$ group, $R^{79}$ being a $C_1$-$C_6$ alkyl, a $C_1$-$C_6$ haloalkyl, a benzyl, 4-methoxybenzyl or pentafluorophenyl;

comprising a deprotection reaction, in an acidic or in a basic medium, of a compound of general formula (IX) to provide an amine derivative of general formula (II) or one of its salt.

A seventh example (G) of such a process may be when:

$R^a$, X, n are as defined above;

$R^1$ is a hydroxy group; and $R^3$, $R^2$, and $R^4$ are hydrogen atoms;

then, the amine derivative of general formula (II) may be prepared according to a process comprising:

a first step according to reaction scheme G-1:

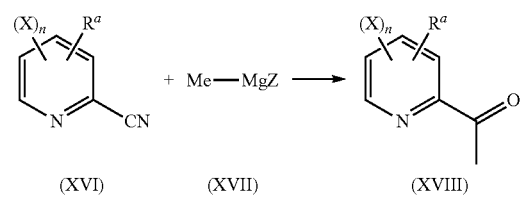

Scheme G-1

(XVI)  (XVII)  (XVIII)

in which: —$R^a$, X and n are as defined above;

Z is a halogen atom;

comprising the addition of a methyl magnesium halogenide of general formula (XVII) on a pyridine derivative of general formula (XVI) to provide a compound of general formula (XVIII);

a second step according to reaction scheme G-2:

Scheme G-2

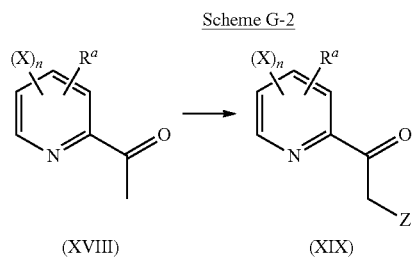

(XVIII) → (XIX)

in which: —$R^a$, X and n are as defined above;

Z is a halogen atom;

comprising the halogenation of a compound of general formula (XVIII) into a compound of general formula (XIX) by use of a halogenating agent such as chlorine, bromine, hypochlorite ions, hypobromite ions, trichloride ions, tribromide ions, N-chloro imides, N-chloro amides, N-chloro amines, N-bromo imides, N-bromo amides or N-bromo amines;

a third step according to reaction scheme G-3:

Scheme G-3

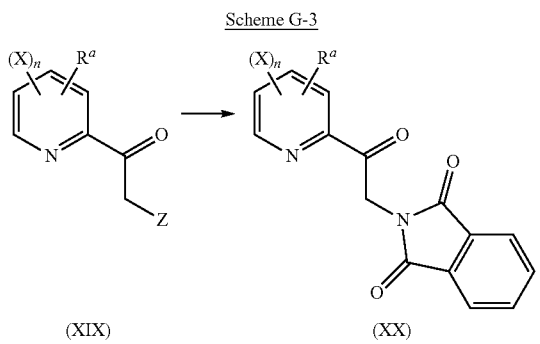

(XIX) → (XX)

in which: —$R^a$, X and n are as defined above;

Z is a halogen atom;

comprising the nucleophilic substitution of a compound of general formula (XIX) by a phthalimide salt to produce a compound of general formula (XX);

a fourth step according to reaction scheme G-4:

Scheme G-4

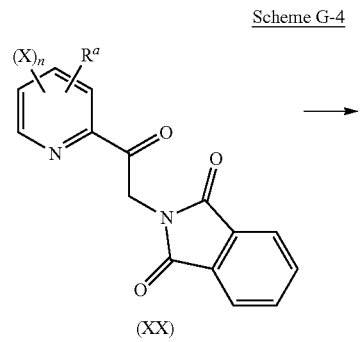

(XX)

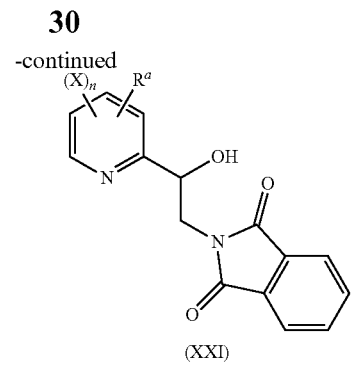

(XXI)

in which $R^a$, X and n are as defined above;

comprising the reduction of a compound of general formula (XX) by a hydride donor to produce a compound of general formula (XXI);

a fifth step according to reaction scheme G-5:

Scheme G-5

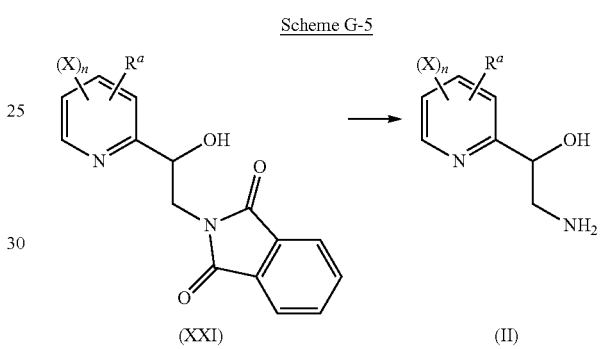

(XXI) → (II)

in which $R^a$, X and n are as defined above;

comprising the de-protection of a compound of general formula (XXI) by reacting it with hydrazine hydrate or a hydrazine salt to provide an amine derivative of general formula (II) or one of its salt;

Compounds according to the present invention can be prepared according to the above described processes. It will nevertheless be understood that, on the basis of his general knowledge and of available publications, the skilled worker will be able to adapt these processes according to the specifics of each of the compounds which it is desired to synthesise.

The present invention also relates to a fungicidal composition comprising an effective amount of an active material of general formula (I). Thus, according to the present invention, there is provided a fungicidal composition comprising, as an active ingredient, an effective amount of a compound of general formula (I) as defined above and an agriculturally acceptable support, carrier or filler.

In the present specification, the term "support" denotes a natural or synthetic, organic or inorganic material with which the active material is combined to make it easier to apply, notably to the parts of the plant. This support is thus generally inert and should be agriculturally acceptable. The support may be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The composition may also comprise additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active material and/or the inert support are water-insoluble and when the vector agent for the application is water. Preferably, surfactant content may be comprised between 5% and 40% by weight of the composition.

Optionally, additional components may also be included, e.g. protective colloids, adhesives, thickeners, thixotropic agents, penetration agents, stabilisers, sequestering agents. More generally, the active materials can be combined with any solid or liquid additive, which complies with the usual formulation techniques.

In general, the composition according to the invention may contain from 0.05 to 99% (by weight) of active material, preferably 10 to 70% by weight.

Compositions according to the present invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ulv) liquid, ultra low volume (ulv) suspension, water dispersible granules or tablets, water dispersible powder for slurry treatment, water soluble granules or tablets, water soluble powder for seed treatment and wettable powder.

These compositions include not only compositions which are ready to be applied to the plant or seed to be treated by means of a suitable device, such as a spraying or dusting device, but also concentrated commercial compositions which must be diluted before application to the crop.

The compounds of the invention can also be mixed with one or more insecticides, fungicides, bactericides, attractant acaricides or pheromones or other compounds with biological activity. The mixtures thus obtained have a broadened spectrum of activity. The mixtures with other fungicides are particularly advantageous.

The fungicidal compositions of the present invention can be used to curatively or preventively control the phytopathogenic fungi of crops. Thus, according to a further aspect of the present invention, there is provided a method for curatively or preventively controlling the phytopathogenic fungi of crops characterised in that a fungicidal composition as hereinbefore defined is applied to the seed, the plant and/or to the fruit of the plant or to the soil in which the plant is growing or in which it is desired to grow.

The composition as used against phytopathogenic fungi of crops comprises an effective and non-phytotoxic amount of an active material of general formula (I).

The expression "effective and non-phytotoxic amount" means an amount of composition according to the invention which is sufficient to control or destroy the fungi present or liable to appear on the crops, and which does not entail any appreciable symptom of phytotoxicity for the said crops. Such an amount can vary within a wide range depending on the fungus to be controlled, the type of crop, the climatic conditions and the compounds included in the fungicidal composition according to the invention.

This amount can be determined by systematic field trials, which are within the capabilities of a person skilled in the art.

The method of treatment according to the present invention is useful to treat propagation material such as tubers or rhizomes, but also seeds, seedlings or seedlings pricking out and plants or plants pricking out. This method of treatment can also be useful to treat roots. The method of treatment according to the present invention can also be useful to treat the overground parts of the plant such as trunks, stems or stalks, leaves, flowers and fruits of the concerned plant.

Among the plants that can be protected by the method according to the invention, mention may be made of cotton; flax; vine; fruit crops such as Rosaceae sp. (for instance pip fruits such as apples and pears, but also stone fruits such as apricots, almonds and peaches), Ribesioidae sp., Juglandaceae sp., Betulaceae sp., Anacardiaceae sp., Fagaceae sp., Moraceae sp., Oleaceae sp., Actimidaceae sp., Lauraceae sp., Musaceae sp. (for instance banana trees and plantins), Rubiaceae sp., Theaceae sp., Sterculiceae sp., Rutaceae sp. (for instance lemons, oranges and grapefruits); leguminous crops such as Solanaceae sp. (for instance tomatoes), Liliaceae sp., Asteraceae sp. (for instance lettuces), Umbelliferae sp., Cruciferae sp., Chenopodiaceae sp., Cucurbitaceae sp., Papilionaceae sp. (for instance peas), Rosaceae sp. (for instance strawberries); big crops such as Graminae sp. (for instance maize, cereals such as wheat, rice, barley and triticale), Asteraceae sp. (for instance sunflower), Cruciferae sp. (for instance colza), Papilionaceae sp. (for instance soja), Solanaceae sp. (for instance potatoes), Chenopodiaceae sp. (for instance beetroots); horticultural and forest crops; as well as genetically modified homologues of these crops.

Among the plants and the possible diseases of these plants protected by the method according to the present invention, mention may be made of:
wheat, as regards controlling the following seed diseases: fusaria (*Microdochium nivale* and *Fusarium roseum*), stinking smut (*Tilletia caries, Tilletia controversa* or *Tilletia indica*), septoria disease (*Septoria nodorum*) and loose smut;
wheat, as regards controlling the following diseases of the aerial parts of the plant: cereal eyespot (*Tapesia yallundae, Tapesia acuiformis*), take-all (*Gaeumannomyces graminis*), foot blight (*F. culmorum, F. graminearum*), black speck (*Rhizoctonia cerealis*), powdery mildew (*Erysiphe graminis forma* specie *tritici*), rusts (*Puccinia striiformis* and *Puccinia recondita*) and septoria diseases (*Septoria tritici* and *Septoria nodorum*);
wheat and barley, as regards controlling bacterial and viral diseases, for example barley yellow mosaic;
barley, as regards controlling the following seed diseases: net blotch (*Pyrenophora graminea, Pyrenophora teres* and *Cochliobolus sativus*), loose smut (*Ustilago nuda*) and fusaria (*Microdochium nivale* and *Fusarium roseum*);
barley, as regards controlling the following diseases of the aerial parts of the plant: cereal eyespot (*Tapesia yallundae*), net blotch (*Pyrenophora teres* and *Cochliobolus sativus*), powdery mildew (*Erysiphe graminis forma* specie *hordei*), dwarf leaf rust (*Puccinia hordei*) and leaf blotch (*Rhynchosporium secalis*);
potato, as regards controlling tuber diseases (in particular *Helminthosporium solani, Phoma tuberosa, Rhizocto-* nia solani, Fusarium solani), mildew (Phytopthora infestans) and certain viruses (virus Y);

potato, as regards controlling the following foliage diseases: early blight (Alternaria solani), mildew (Phytophthora infestans);

cotton, as regards controlling the following diseases of young plants grown from seeds: damping-off and collar rot (Rhizoctonia solani, Fusarium oxysporum) and black root rot (Thielaviopsis basicola);

protein yielding crops, for example peas, as regards controlling the following seed diseases: anthracnose (Ascochyta pisi, Mycosphaerella pinodes), fusaria (Fusarium oxysporum), grey mould (Botrytis cinerea) and mildew (Peronospora pisi);

oil-bearing crops, for example rape, as regards controlling the following seed diseases: Phoma lingam, Alternaria brassicae and Sclerotinia sclerotiorum;

corn, as regards controlling seed diseases: (Rhizopus sp., Penicillium sp., Trichoderma sp., Aspergillus sp., and Gibberella fujikuroi);

flax, as regards controlling the seed disease: Alternaria linicola;

forest trees, as regards controlling damping-off (Fusarium oxysporum, Rhizoctonia solani);

rice, as regards controlling the following diseases of the aerial parts: blast disease (Magnaporthe grisea), bordered sheath spot (Rhizoctonia solani);

leguminous crops, as regards controlling the following diseases of seeds or of young plants grown from seeds: damping-off and collar rot (Fusarium oxysporum, Fusarium roseum, Rhizoctonia solani, Pythium sp.);

leguminous crops, as regards controlling the following diseases of the aerial parts: grey mould (Botrytis sp.), powdery mildews (in particular Erysiphe cichoracearum, Sphaerotheca fuliginea and Leveillula taurica), fusaria (Fusarium oxysporum, Fusarium roseum), leaf spot (Cladosporium sp.), alternaria leaf spot (Alternaria sp.), anthracnose (Colletotrichum sp.), septoria leaf spot (Septoria sp.), black speck (Rhizoctonia solani), mildews (for example Bremia lactucae, Peronospora sp., Pseudoperonospora sp., Phytophthora sp.);

fruit trees, as regards diseases of the aerial parts: monilia disease (Monilia fructigenae, M. laxa), scab (Venturia inaequalis), powdery mildew (Podosphaera leucotricha);

vine, as regards diseases of the foliage: in particular grey mould (Botrytis cinerea), powdery mildew (Uncinula necator), black rot (Guignardia biwelli) and mildew (Plasmopara viticola);

beetroot, as regards the following diseases of the aerial parts: cercospora blight (Cercospora beticola), powdery mildew (Erysiphe beticola), leaf spot (Ramularia beticola).

The fungicide composition according to the present invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds of the present invention, or a composition according to the invention; this includes for example direct application, spraying, dipping, injection or any other suitable means.

The dose of active material usually applied in the treatment according to the present invention is generally and advantageously between 10 and 800 g/ha, preferably between 50 and 300 g/ha for applications in foliar treatment. The dose of active substance applied is generally and advantageously between 2 and 200 g per 100 kg of seed, preferably between 3 and 150 g per 100 kg of seed in the case of seed treatment. It is clearly understood that the doses indicated above are given as illustrative examples of the invention. A person skilled in the art will know how to adapt the application doses according to the nature of the crop to be treated.

The fungicidal composition according to the present invention may also be used in the treatment of genetically modified organisms with the compounds according to the invention or the agrochemical compositions according to the invention. Genetically modified plants are plants into whose genome a heterologous gene encoding a protein of interest has been stably integrated. The expression "heterologous gene encoding a protein of interest" essentially means genes which give the transformed plant new agronomic properties, or genes for improving the agronomic quality of the transformed plant.

The compositions according to the present invention may also be used for the preparation of composition useful to curatively or preventively treat human and animal fungal diseases such as, for example, mycoses, dermatoses, trichophyton diseases and candidiases or diseases caused by Aspergillus spp., for example Aspergillus fumigatus.

The aspects of the present invention will now be illustrated with reference to the following tables of compounds and examples. The following Tables A to V illustrate in a non-limiting manner examples of fungicidal compounds according to the present invention. In the following Examples, M+1 (or M−1) means the molecular ion peak, plus or minus 1 a.m.u. (atomic mass units) respectively, as observed in mass spectroscopy.

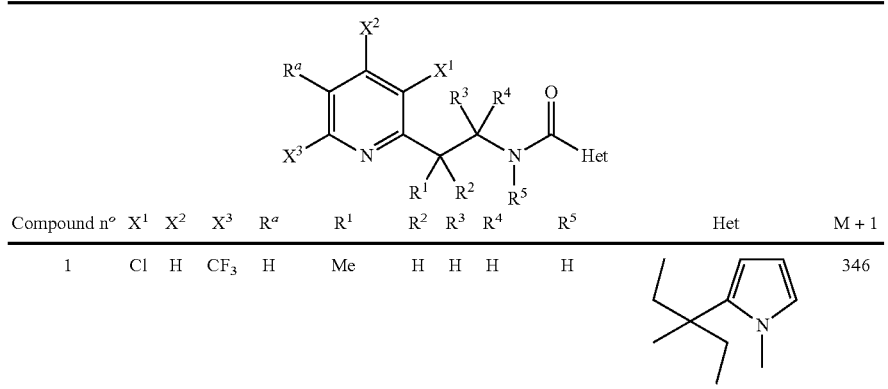

| Compound n° | $X^1$ | $X^2$ | $X^3$ | $R^a$ | $R^1$ | $R^2$ | $R^3$ | $R^4$ | $R^5$ | Het | M + 1 |
|---|---|---|---|---|---|---|---|---|---|---|---|
| 1 | Cl | H | $CF_3$ | H | Me | H | H | H | H | | 346 |

-continued
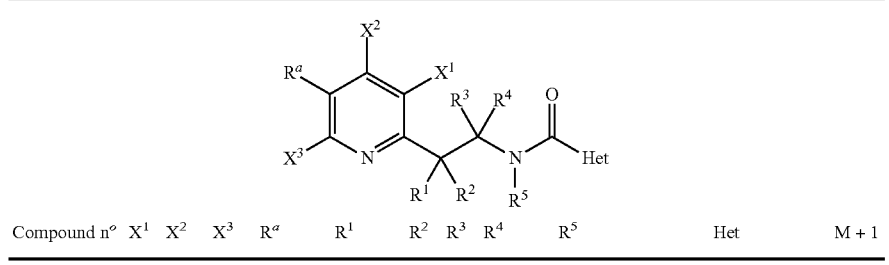
| Compound n° | X¹ | X² | X³ | Rᵃ | R¹ | R² | R³ | R⁴ | R⁵ | Het | M + 1 |
|---|---|---|---|---|---|---|---|---|---|---|---|
| 2 | Cl | H | CF₃ | H | Me | H | H | H | H | 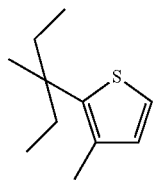 | 404 |
| 3 | Cl | H | CF₃ | H | Me | H | H | H | H | 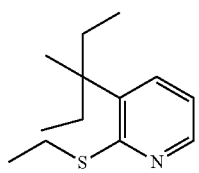 | 377 |
| 4 | Cl | H | CF₃ | H | Et | H | H | H | H | 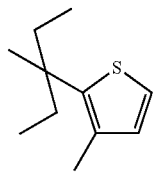 | 419 |
| 5 | Cl | H | CF₃ | H | Et | H | H | H | H | 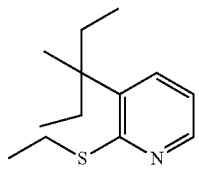 | 360 |
| 6 | Cl | H | CF₃ | H | Et | H | H | H | H | 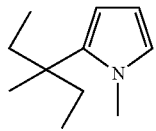 | 378 |
| 7 | Cl | H | CF₃ | H | Me | H | H | H | H | 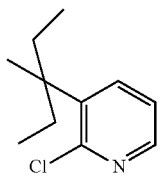 | 392 |
| 8 | Cl | H | CF₃ | H | Me | Me | H | H | H | 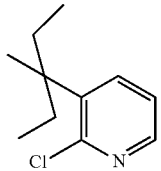 | 406 |

-continued

| Compound n° | X¹ | X² | X³ | Rᵃ | R¹ | R² | R³ | R⁴ | R⁵ | Het | M+1 |
|---|---|---|---|---|---|---|---|---|---|---|---|
| 9 | Cl | H | CF₃ | H | Me | Et | H | H | H | 3-(3-pentyl)-2-chloropyridinyl | 447 |
| 10 | Cl | H | CF₃ | H | Pr | Pr | H | H | H | 3-(3-pentyl)-2-chloropyridinyl | 428 |
| 11 | Cl | H | CF₃ | H | Et | H | H | H | H | 5-(3-pentyl)-2-methyl-4-(difluoromethyl)thiazolyl | 411 |
| 12 | Cl | H | CF₃ | H | Et | H | H | H | H | 4-(3-pentyl)-1-methyl-3-(difluoromethyl)pyrazolyl | 395 |
| 13 | Cl | H | CF₃ | H | Et | H | H | H | H | (3-pentyl)-methyl-oxathiine | 361 |
| 14 | Cl | H | CF₃ | H | Et | H | H | H | H | 3-(3-pentyl)-2-methylfuryl | 446 |
| 15 | Cl | H | CF₃ | H | Et | H | H | H | H | 5-(3-pentyl)-2-methyl-4-(trifluoromethyl)thiazolyl | 429 |
| 16 | Cl | H | CF₃ | H | Et | H | H | H | H | 4-(3-pentyl)-1-methyl-3-(trifluoromethyl)pyrazolyl | 442 |

-continued
| Compound n° | X¹ | X² | X³ | Rᵃ | R¹ | R² | R³ | R⁴ | R⁵ | Het | M + 1 |
|---|---|---|---|---|---|---|---|---|---|---|---|
| 17 | Cl | H | CF₃ | H | Pr | H | H | H | H | 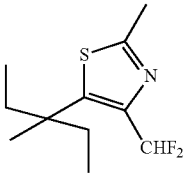 | 425 |
| 18 | Cl | H | CF₃ | H | Pr | H | H | H | H | 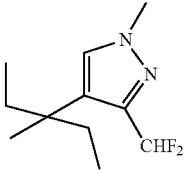 | 408 |
| 19 | Cl | H | CF₃ | H | Pr | H | H | H | H | 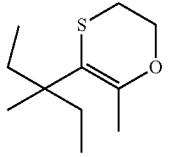 | 406 |
| 20 | Cl | H | CF₃ | H | Pr | H | H | H | H | 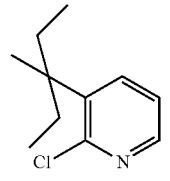 | 374 |
| 21 | Cl | H | CF₃ | H | Pr | H | H | H | H | 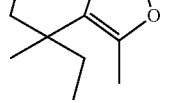 | 460 |
| 22 | Cl | H | CF₃ | H | Pr | H | H | H | H | 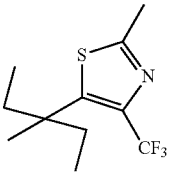 | 442 |
| 23 | Cl | H | CF₃ | H | Pr | H | H | H | H | 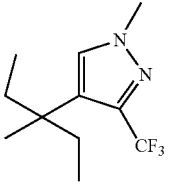 | 395 |

-continued

| Compound n° | X¹ | X² | X³ | Rᵃ | R¹ | R² | R³ | R⁴ | R⁵ | Het | M + 1 |
|---|---|---|---|---|---|---|---|---|---|---|---|
| 24 | Cl | H | CF₃ | H | Me | Me | H | H | H | | 429 |
| 25 | Cl | H | CF₃ | H | Me | Me | H | H | H | | 411 |
| 26 | Cl | H | CF₃ | H | Me | Me | H | H | H | | 446 |
| 27 | Cl | H | CF₃ | H | Me | Me | H | H | H | | 475 |
| 28 | Cl | H | CF₃ | H | Me | H | H | H | H | | 381 |
| 29 | Cl | H | CF₃ | H | Me | H | H | H | H | | 415 |
| 30 | Cl | H | CF₃ | H | Me | H | H | H | H | | 397 |

-continued
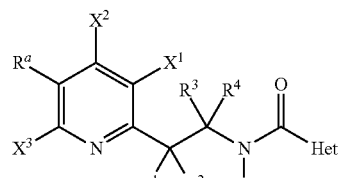
| Compound n° | X¹ | X² | X³ | R$^a$ | R¹ | R² | R³ | R⁴ | R⁵ | Het | M + 1 |
|---|---|---|---|---|---|---|---|---|---|---|---|
| 31 | Cl | H | CF$_3$ | H | Me | H | H | H | H | 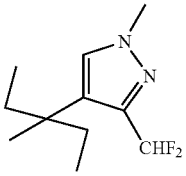 | 392 |
| 32 | Cl | H | CF$_3$ | H | H | H | Et | H | H | 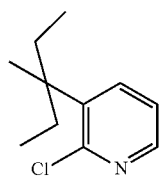 | 489 |
| 33 | Cl | H | CF$_3$ | H | H | H | Et | H | H | 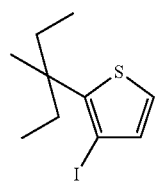 | 449 |
| 34 | Cl | H | CF$_3$ | H | H | H | Et | H | H | 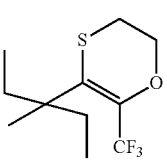 | 395 |
| 35 | Cl | H | CF$_3$ | H | H | H | Et | H | H | 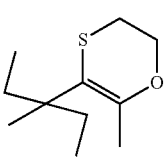 | 363 |
| 36 | Cl | H | CF$_3$ | H | NHCOMe | H | H | H | H | 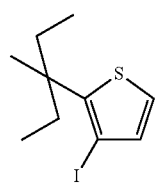 | 518 |
| 37 | Cl | H | CF$_3$ | H | H | H | Ph | H | H | 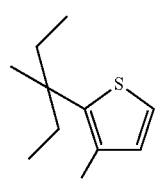 | 537 |
| 38 | Cl | H | CF$_3$ | H | H | H | Ph | H | H | 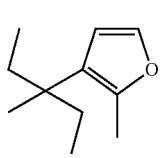 | 409 |

-continued
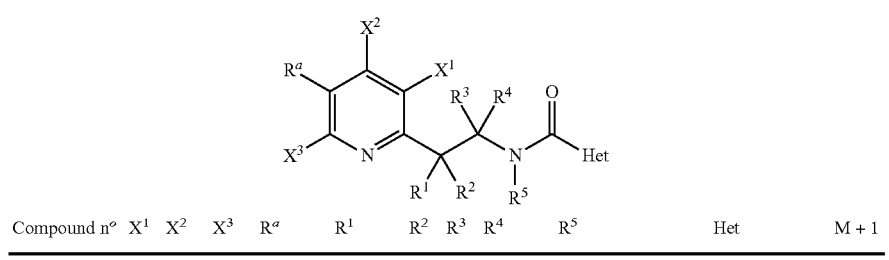
| Compound n° | X¹ | X² | X³ | Rᵃ | R¹ | R² | R³ | R⁴ | R⁵ | Het | M + 1 |
|---|---|---|---|---|---|---|---|---|---|---|---|
| 39 | Cl | H | CF₃ | H | H | H | Ph | H | H | 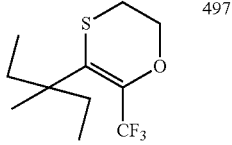 | 497 |
| 40 | Cl | H | CF₃ | H | H | H | Ph | H | H | 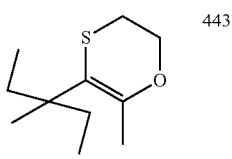 | 443 |
| 41 | Cl | H | CF₃ | H | H | H | Ph | H | H | 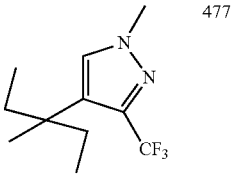 | 477 |
| 42 | Cl | H | CF₃ | H | H | H | Ph | H | H | 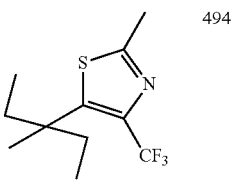 | 494 |
| 43 | Cl | H | CF₃ | H | NHCOMe | H | H | H | H | 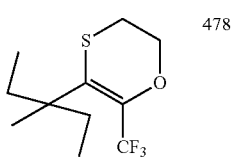 | 478 |
| 44 | Cl | H | CF₃ | H | NHCO-2,6-dichloro-phenyl | H | H | H | H | 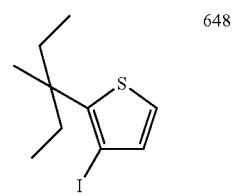 | 648 |
| 45 | Cl | H | CF₃ | H | NHCO-2,6-dichloro-phenyl | H | H | H | H | 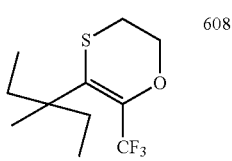 | 608 |

-continued
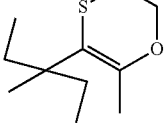
| Compound n° | X¹ | X² | X³ | Rᵃ | R¹ | R² | R³ | R⁴ | R⁵ | Het | M + 1 |
|---|---|---|---|---|---|---|---|---|---|---|---|
| 46 | Cl | H | CF₃ | H | NHCO-2,6-dichloro-phenyl | H | H | H | H | 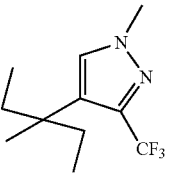 | 554 |
| 47 | Cl | H | CF₃ | H | NHCO-2,6-dichloro-phenyl | H | H | H | H | 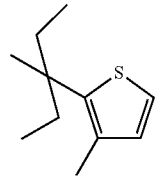 | 588 |
| 48 | Cl | H | CF₃ | H | NHCO-2,6-dichloro-phenyl | H | H | H | H | 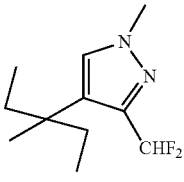 | 536 |
| 49 | Cl | H | CF₃ | H | NHCO-2,6-dichloro-phenyl | H | H | H | H | 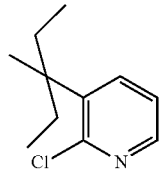 | 570 |
| 50 | Cl | H | CF₃ | H | Me | H | Me | H | H | 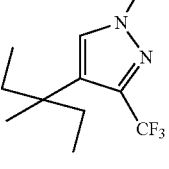 | 392 |
| 51 | Cl | H | CF₃ | H | Me | H | Me | H | H | 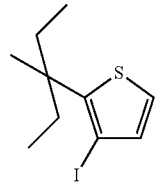 | 429 |
| 52 | Cl | H | CF₃ | H | Me | H | Me | H | H |  | 489 |

-continued

| Compound n° | X¹ | X² | X³ | Rᵃ | R¹ | R² | R³ | R⁴ | R⁵ | Het | M + 1 |
|---|---|---|---|---|---|---|---|---|---|---|---|
| 53 | Cl | H | CF₃ | H | Me | H | Me | H | H | | 449 |
| 54 | Cl | H | CF₃ | H | Me | H | Me | H | H | | 395 |
| 55 | Cl | H | CF₃ | H | H | H | Me | H | Cyclopropyl | | 515 |
| 56 | H | H | CF₃ | H | Me | H | H | H | H | | 398 |
| 57 | H | H | CF₃ | H | Me | H | H | H | H | | 381 |
| 58 | H | H | CF₃ | H | Me | H | H | H | H | | 441 |
| 59 | Hl | Cl | CF₃ | H | Me | H | H | H | H | | 379 |

-continued

| Compound n° | X¹ | X² | X³ | Rᵃ | R¹ | R² | R³ | R⁴ | R⁵ | Het | M + 1 |
|---|---|---|---|---|---|---|---|---|---|---|---|
| 60 | Cl | H | CF₃ | H | NHCO-(2-chloro-phenyl) | H | H | H | H | 3-iodo-2-(pent-3-yl)thiophene | 614 |
| 61 | Cl | H | CF₃ | H | NHCO-(2-chloro-phenyl) | H | H | H | H | 2-methyl-5-(pent-3-yl)-4-(trifluoromethyl)thiazole | 571 |
| 62 | Cl | H | CF₃ | H | NHCO-(2-chloro-phenyl) | H | H | H | H | 2-methyl-3-(pent-3-yl)-5,6-dihydro-1,4-oxathiine | 520 |

EXAMPLES OF PROCESS FOR THE PREPARATION OF THE COMPOUND OF GENERAL FORMULA (I)

Example 1

Preparation of N-{2-[3-chloro-5-(trifluoromethyl)-2-pyridinyl]butyl}-1-methyl-3-(trifluoromethyl)-1H-pyrazole-4-carboxamide (compound 15)

100 mg of 2-[3-chloro-5-(trifluoromethyl)-2-pyridinyl]-1-butanamine (0.0004 mol), 60 mg of 1-methyl-3-(trifluoromethyl)-1H-pyrazole-4-carboxylic acid (0.0004 mol), 0.109 g of 4-(4,6-dimethoxy[1.3.5]triazin-2-yl)-4-methylmorpholinium chloride hydrate (0.0004 mol) are stirred in 2 mL of ethanol at room temperature overnight.

The reaction mixture is concentrated to dryness and purified on silica to yield to 95 mg of N-{2-[3-chloro-5-(trifluoromethyl)-2-pyridinyl]butyl}-1-methyl-3-(trifluoromethyl)-1H-pyrazole-4-carboxamide (57%).

Mass spectrum: [M+1]=429.

Example 2

Preparation of N-{2-[3-chloro-5-(trifluoromethyl)-2-pyridinyl]-2-methylpropyl}-1-methyl-3-(trifluoromethyl)-1H-pyrazole-4-carboxamide (compound 24)

104 mg of 2-[3-chloro-5-(trifluoromethyl)-2-pyridinyl]-2-methyl-1-propanamine hydrochloride, 40 μL of triethylamine, 62 mg of 3-(trifluoromethyl)-1H-pyrazole-4-carboxylic acid, 0.13 g of 4-(4,6-dimethoxy[1.3.5]triazin-2-yl)-4-methylmorpholinium chloride hydrate (0.00054 mol) are stirred in 2 mL of methanol at room temperature overnight.

The reaction mixture is concentrated to dryness and purified on silica to yield to 95 mg of N-{2-[3-chloro-5-(trifluoromethyl)-2-pyridinyl]-2-methylpropyl}-1-methyl-3-(trifluoromethyl)-1H-pyrazole-4-carboxamide (59%).

Mass spectrum: [M+1]=429.

Example 3

Preparation of N-(1-{[3-chloro-5-(trifluoromethyl)-2-pyridinyl]methyl}propyl)-3-iodo-2-thiophenecarboxamide (compound 32)

100 mg of 1-[3-chloro-5-(trifluoromethyl)-2-pyridinyl]-2-butanamine (0.0004 mol), 107 mg of 3-Iodo-thiophene-2-carboxylic acid (0.0004 mol,), 83 mg of 4-(4,6-dimethoxy[1.3.5]triazin-2-yl)-4-methylmorpholinium chloride hydrate (0.0003 mol) are stirred in 2 mL of ethanol at room temperature overnight.

The reaction mixture is concentrated to dryness and purified on silica to yield to 96 mg of N-(1-{[3-chloro-5-(trifluoromethyl)-2-pyridinyl]methyl}propyl)-3-iodo-2-thiophenecarboxamide (54%).

Mass spectrum: [M+1]=489.

Example 4

Preparation of N-{2-[3-chloro-5-(trifluoromethyl)-2-pyridinyl]-1-phenylethyl}-3-iodo-2-thiophenecarboxamide (compound 37)

79 mg of 2-[3-chloro-5-(trifluoromethyl)-2-pyridinyl]-1-phenylethanamine (0.0003 mol), 76 mg of 3-Iodo-thiophene-2-carboxylic acid (0.0003 mol), 83 mg of 4-(4,6-dimethoxy

[1.3.5]triazin-2-yl)-4-methylmorpholinium chloride hydrate (0.0003 mol) are stirred in 3 mL of ethanol at room temperature overnight.

The reaction mixture is concentrated to dryness and purified on silica to yield to 27 mg of N-{2-[3-chloro-5-(trifluoromethyl)-2-pyridinyl]-1-phenylethyl}-3-iodo-2-thiophenecarboxamide.

mass spectrum: [M+1]=537.

Example 5

Preparation of N-{2-(acetylamino)-2-[3-chloro-5-(trifluoromethyl)-2-pyridinyl]ethyl}-3-iodo-2-thiophenecarboxamide (compound 36)

108 mg of N-{2-amino-1-[3-chloro-5-(trifluoromethyl)-2-pyridinyl]ethyl}acetamide trifluoroacetate (0.0003 mol), 76 mg of 3-Iodo-thiophene-2-carboxylic acid (0.0003 mol), 83 mg of 4-(4,6-dimethoxy[1.3.5]triazin-2-yl)-4-methylmorpholinium chloride hydrate (0.0003 mol), 41 µL of triethylamine (0.0003 mol) are stirred in 3 mL of ethanol at room temperature overnight. The reaction mixture is concentrated to dryness and purified on silica to yield to 29 mg of N-{2-(acetylamino)-2-[3-chloro-5-(trifluoromethyl)-2-pyridinyl]ethyl}-3-iodo-2-thiophenecarboxamide.

Mass spectrum: [M+1]=518.

Examples of Process for the Preparation of Starting Material (Intermediates of General Formula II)

Example 6

Preparation of 2-[3-chloro-5-(trifluoromethyl)-2-pyridinyl]-1-phenylethanamine

Preparation of 2-[3-chloro-5-(trifluoromethyl)-2-pyridinyl]-1-phenylethanone

To a suspension of 2.6 g (0.065 mol) of sodium hydride 60% in dimethoxyethane at room temperature is added 3.4 mL (0.029 mol) of acetophenone. After 45 min., 5.55 mL (0.038 mol) of 2,3-dichloro-5-(trifluoromethyl)pyridine is added. After 25 min., the reaction mixture is poured over 100 mL of hydrochloric acid 1N, extracted twice with 100 mL of ethyl acetate.

The organic phase is washed twice 100 mL of water, dried over magnesium sulfate, filtered and concentrated to provide 15 g of crude material which is purified over a column of silica by using a mixture of heptane and ethyl acetate as eluent, to yield to 5.74 g of desired product 2-[3-chloro-5-(trifluoromethyl)-2-pyridinyl]-1-phenylethanone (74%).

RMN $^1$H δ (ppm) 8.73; (1H, s); 7.95 (1H, s); 7.45 (2H, m); 7.42 (2H, m); 4.75 (2H, s).

Preparation of 2-[3-chloro-5-(trifluoromethyl)-2-pyridinyl]-1-phenylethanamine 5.6 g (0.0187 mol) of 2-[3-chloro-5-(trifluoromethyl)-2-pyridinyl]-1-phenylethanone are diluted in 50 mL of methanol. 50 g of molecular sieves 3 Å, 14.4 g (0.187 mol) of ammonium acetate and 2.45 g (0.037 mol) of sodium cyanoborohydride are then consequently added. The pH is adjusted to 5-6 with acetic acid (1 mL). After 4 days of reaction at room temperature, the medium is filtered and 1M aqueous sodium hydroxide is added until pH=12. 150 mL of ethyl acetate are added, after separation, the aqueous phase is extracted twice with 150 mL of ethyl acetate.

The organic phase is washed with 100 mL of brine, 100 mL of water; dried over magnesium sulfate, filtered and concentrated to yield to 1.3 g of desired product 2-[3-chloro-5-(trifluoromethyl)-2-pyridinyl]-1-phenylethanamine (23%).

Mass spectrum: [M+1]=301.

Example 7

Preparation of 2-[3-chloro-5-(trifluoromethyl)-2-pyridinyl]-1-butanamine hydrochloride Preparation of methyl [3-chloro-5-(trifluoromethyl)-2-pyridinyl](cyano)acetate Under argon, 116 g of sodium hydride 60% in dispersion in oil (2.91 mol, 1.8 eq.) was suspended in 3 L of DMF. The suspension was cooled down in an ice-water bath. 160 g (1.616 mol, 1.0 eq) of methyl cyanoacetate in solution in 200 mL of DMF was added dropwise under stirring. Temperature rose to 50° C. and hydrogen was released. Once bubbling was over, 350 g (1.616 mol, 1.0 eq) of 2,3-dichloro-5-(trifluoromethyl)-pyridine was added under stirring. The mixture was stirred overnight at room temperature. 50 mL of methanol were added dropwise to quench the reaction. The reaction mixture was poured in 5 L of water. pH was adjusted to 3-4 with concentrated hydrochloric acid.

The yellow precipitate which formed was filtered and washed thoroughly with water and pentane. 414 g of methyl [3-chloro-5-(trifluoromethyl)-2-pyridinyl](cyano)acetate (92%) were recovered.

Mass spectrum: [M+1]=279.

Preparation of [3-chloro-5-(trifluoromethyl)-2-pyridinyl]acetonitrile 314 g (1.13 mol, 1 eq.) of methyl [3-chloro-5-(trifluoromethyl)-2-pyridinyl](cyano)acetate and 22 g (0.38 mol, 0.33 eq.) of sodium chloride were dissolved in mixture of 44 mL of water and 1.1 L of DMSO. The reaction mixture was stirred and heated to 160° C. Gases were released, once the bubbling was over, the reaction was allowed to come back to room temperature under stirring. 1 L of water and 0.5 L of dichloromethane were added. After separation, the aqueous phase was extracted twice with 0.5 L of DCM.

The organic phase was extracted twice with 0.5 L of water and dried over magnesium sulfate. After concentration, the crude product was diluted in 100 mL of DCM and eluted with EtOAc/Heptane (20/80) over a bed of silica. The filtrate was concentrated to yield 227 g of [3-chloro-5-(trifluoromethyl)-2-pyridinyl]acetonitrile (91%).

Mass spectrum: [M+1]=223.

Preparation of 2-[3-chloro-5-(trifluoromethyl)-2-pyridinyl]butanenitrile 199 g (0.9 mol) of 3 of [3-chloro-5-(trifluoromethyl)-2-pyridinyl]acetonitrile are dissolved in 3 L of THF at −5° C. A solution of 106 g (0.945 mol) of potassium terbutanoate in 0.6 L of THF is slowly added to the reaction medium. After 2H, 147 g (0.945 mol) of ethyl iodide is added dropwise to the reaction mixture which is stirred overnight at room temperature. 3 L of water and 2 L of ethyl acetate are added to the reaction mixture, after separation, the aqueous phase is extracted twice with 500 mL of ethyl acetate.

The organic phase is washed with 4 L of brine, 1 L of water, dried over magnesium sulfate, concentrated to yield to 223 g of desired product 2-[3-chloro-5-(trifluoromethyl)-2-pyridinyl]butanenitrile (100%).

RMN $^1$H δ (ppm) 8.7 (1H, d, J=1.5 Hz); 7.91 (1H, d, J=1.5 Hz); 4.37 (1H, dd, J=6.57 Hz-7.83 Hz); 2.00 (2H, m); 1.06 (3H, t, J=7.33 Hz).

Preparation of tert-butyl 2-[3-chloro-5-(trifluoromethyl)-2-pyridinyl]butylcarbamate 189 g of 2-[3-chloro-5-(trifluoromethyl)-2-pyridinyl]butanenitrile (0.758 mol), 331 g (1.51 mol) of diterbutyl carbonate, 198 g (0.834 mol) of nickel chloride (II)-hexahydrate are stirred in 2 L of methanol at room temperature. 200.6 g (5.31 mol) of sodium borohydride are added portionwise. After 3 hours of stirring, the reaction mixture is filtered over Supercel, 2 L of ethyl acetate are added, followed by 1.5 L of an aqueous solution of sodium bicarbonate.

After separation, the organic phase is washed thrice with 1 L of an aqueous solution of sodium bicarbonate, dried over magnesium sulfate, concentrated to yield to 375 g of crude material which is purified over silica to produce 147 g of desired product tert-butyl 2-[3-chloro-5-(trifluoromethyl)-2-pyridinyl]butylcarbamate (50.5%).

RMN $^1$H δ (ppm) 8.88 (1H, d, J=1.5 Hz); 8.04 (1H, d, J=1.5 Hz); 5.04 (1H, b); 3.78 (1H, m); 3.67 (2H, m); 1.88 (2H, m); 1.34 (9H, s); 1.01 (3H, t, J=7.33 Hz).

Preparation of 2-[3-chloro-5-(trifluoromethyl)-2-pyridinyl]-1-butanamine hydrochloride 146 g of tert-butyl 2-[3-chloro-5-(trifluoromethyl)-2-pyridinyl]butylcarbamate (0.414 mol) are dissolved in 2 L of dichloromethane. 190 mL of trifluoroacetic acid are added dropwise. The reaction mixture is stirred at room temperature for twelve hours, concentrated to dryness and diluted in 300 mL of hydrochloric acid 2M.

After 2H, the reaction mixture is concentrated to dryness to provide 104 g of desired product 2-[3-chloro-5-(trifluoromethyl)-2-pyridinyl]-1-butanamine hydrochloride (87%).

m.p.=139-142° C.

Example 8

Preparation of 1-[3-chloro-5-(trifluoromethyl)-2-pyridinyl]-2-butanamine

Preparation of methyl 2-[3-chloro-5-(trifluoromethyl)-2-pyridinyl]-3-oxopentanoate 4.45 g of potassium hydroxide 85% are suspended in 40 mL of DMF, 4.37 g of methyl 3-oxopentanoate (0.036 mol) are subsequently added. The reaction mixture is warmed to 50° C. and 6 mL of 2,3-dichloro-5-(trifluoromethyl)pyridine are introduced. The reaction mixture is stirred at 50° C. for 4 hours, quenched with 150 mL of an aqueous solution of NaH$_2$PO$_4$ (1M), extracted thrice with 150 mL of ethyl acetate.

The organic phase is washed with 150 mL of brine, 150 mL of water, dried over magnesium sulfate and concentrated to provide 8.8 g of crude material which is purified on silica to yield 2.09 g of desired product methyl 2-[3-chloro-5-(trifluoromethyl)-2-pyridinyl]-3-oxopentanoate (24%).

Mass spectrum: [M+1]=310.

Preparation of 1-[3-chloro-5-(trifluoromethyl)-2-pyridinyl]-2-butanone 2.08 g of methyl 2-[3-chloro-5-(trifluoromethyl)-2-pyridinyl]-3-oxopentanoate (0.00677 mol) and 0.12 g of sodium chloride are dissolved in a mixture of water (0.25 mL) and dimethylsulfoxyde (20 mL). The reaction medium is stirred at a temperature of 130° C. for 8 hours. After cooling, 100 mL of water are added to the reaction mixture which is extracted twice with 150 mL of ethyl acetate.

The organic phase is washed with twice 100 mL of water, dried over magnesium sulfate and concentrated. After a purification on silica, 0.67 g of desired product 1-[3-chloro-5-(trifluoromethyl)-2-pyridinyl]-2-butanone are produced (39%).

Mass spectrum: [M+1]=253.

Preparation of 1-[3-chloro-5-(trifluoromethyl)-2-pyridinyl]-2-butanamine 0.64 g f 1-[3-chloro-5-(trifluoromethyl)-2-pyridinyl]-2-butanone (0.0025 mol) are diluted in 5 mL of methanol. 7.0 g of molecular sieves 3 Å, 1.90 g (0.025 mol) of ammonium acetate and 0.39 g (0.0052 mol) of sodium cyanoborohydride are then consequently added. The reaction medium is stirred overnight at room temperature. After filtration, the pH is adjusted to 9 with an aqueous solution of sodium hydroxide 1 M. The reaction mixture is concentrated to dryness. 30 mL of ethyl acetate are added. The organic phase is washed with an aqueous solution of sodium hydroxide 1 M, brine, and water; dried over magnesium sulfate, filtered and concentrated to dryness. The crude material is dissolved in 15 mL of hydrochloric acid 1M, extracted with 15 mL of ethyl acetate.

The aqueous phase is then basified with an aqueous solution of sodium hydroxide 1 M, extracted thrice with 15 mL of ethyl acetate, dried over magnesium sulfate, filtered and concentrated to dryness to provide 0.21 g of desired product 1-[3-chloro-5-(trifluoromethyl)-2-pyridinyl]-2-butanamine (32%).

Mass spectrum: [M+1]=253.

Example 9

Preparation of N-{2-amino-1-[3-chloro-5-(trifluoromethyl)-2-pyridinyl]ethyl}acetamide trifluoroacetate

Preparation of [3-chloro-5-(trifluoromethyl)-2-pyridinyl][(diphenylmethylene)amino]acetonitrile To a suspension of sodium hydride 60% (4.0 g, 0.1 mol) in dimethylformamide (50 mL) at −10° C. was dropwise added a solution of N-(diphenylmethylene)aminoacetonitrile (11.1 g, 0.05 mol) 60 mL of dimethylformamide. After one hour of stirring is added to the reaction mixture, 7 mL of 2,3-dichloro-5-(trifluoromethyl)pyridine (0.052 mol) are added to the reaction mixture. The reaction medium is allowed to room temperature, stirred for 3 hours, quenched with a mixture of diethyl ether (500 mL) and an aqueous solution of ammonium chloride 10% (500 mL). After separation, the organic phase is dried over magnesium sulfate, filtered and concentrated.

The crude material is purified on silica to yield to 17.8 g of [3-chloro-5-(trifluoromethyl)-2-pyridinyl][(diphenylmethylene)amino]acetonitrile (90%).

m.p.=105-108° C.

Preparation of amino[3-chloro-5-(trifluoromethyl)-2-pyridinyl]acetonitrile hydrochloride 15.0 g of [3-chloro-5-(trifluoromethyl)-2-pyridinyl][(diphenylmethylene)amino]acetonitrile (0.037 mol) are stirred at room temperature for 3 h in a mixture of dichloromethane (15 mL) and hydrochloric acid 10% (15 mL). Phases are separated and the organic phase is washed with 15 mL of hydrochloric acid 10%.

The aqueous phase is concentrated to dryness to provide a pink solid which is washed with diethyl ether, filtered and dried to provide 8.10 g of desired product amino[3-chloro-5-(trifluoromethyl)-2-pyridinyl]acetonitrile hydrochloride (79%).

m.p.=258-260° C.

Preparation of N-[[3-chloro-5-(trifluoromethyl)-2-pyridinyl](cyano)methyl]acetamide 0.67 g of amino[3-chloro-5-(trifluoromethyl)-2-pyridinyl]acetonitrile hydrochloride (0.00245 mol) are dissolved in 15 mL of dichloromethane, 0.68 mL of triethylamine are added. After 10 min. at room temperature, 0.18 mL of acetyl chloride (0.00245 mol) are added, the reaction mixture is stirred overnight. The reaction is quenched with 20 mL of water.

After separation, the organic phase is washed with 20 mL of water, dried on magnesium sulfate, filtered and concentrated to dryness to produce 0.75 g of crude material which is purified on silica to yield 0.54 g of desired product N-[[3-chloro-5-(trifluoromethyl)-2-pyridinyl](cyano)methyl]acetamide (80%).

Mass spectrum: [M+1]=278.

Preparation of tert-butyl 2-(acetylamino)-2-[3-chloro-5-(trifluoromethyl)-2-pyridinyl]ethylcarbamate 5.00 g of N-[[3-chloro-5-(trifluoromethyl)-2-pyridinyl](cyano)methyl]acetamide (0.018 mol), 7.86 g (0.036 mol) of diterbutyl carbonate, 4.28 g (0.018 mol) of nickel chloride (II)-hexahydrate are stirred in 25 mL of methanol at room temperature. 3.40 g (0.09 mol) of sodium borohydride are added portionwise. The reaction mixture is stirred overnight. 200 mL of ethyl acetate are added, followed by 50 mL of water. After separation, the aqueous phase id extracted twice 50 mL of ethyl acetate.

The organic phase is dried over magnesium sulfate, concentrated to yield to 4.01 g of crude material which is purified over silica to produce 1.35 g of desired product tert-butyl 2-(acetylamino)-2-[3-chloro-5-(trifluoromethyl)-2-pyridinyl]ethylcarbamate (19%).

Mass spectrum: [M+1]=382.

Preparation of N-{2-amino-1-[3-chloro-5-(trifluoromethyl)-2-pyridinyl]ethyl}acetamide trifluoroacetate 1.30 g of tert-butyl 2-(acetylamino)-2-[3-chloro-5-(trifluoromethyl)-2-pyridinyl]ethylcarbamate (0.034 mol) are diluted in a mixture of dichloromethane (2.5 mL) and trifluoroacetic acid (2.5 mL). After stirring overnight at room temperature, the reaction mixture is concentrated to dryness to yield to 1.34 g of desired product N-{2-amino-1-[3-chloro-5-(trifluoromethyl)-2-pyridinyl]ethyl}acetamide trifluoroacetate (99%).

Mass spectrum: [M+1−HCl]=282.

Example 10

Preparation of 2-amino-1-[3-chloro-5-(trifluoromethyl)-2-pyridinyl]ethanol

Preparation of 1-[3-chloro-5-(trifluoromethyl)-2-pyridinyl]ethanone

To 225 ml of dry toluene were added 210 ml (0.29 mol) of a 1.4 M solution of methylmagnesium bromide in toluene/tetrahydrofuran 75:25. The solution was cooled to −5° C. and 30 g (0.145 mol) of 3-chloro-5-(trifluoromethyl)-2-pyridinecarbonitrile, were slowly added in 2 hours at 0° C. After addition, the dark solution was further stirred at room temperature for 5 hours. The reaction mixture was neutralized by 350 ml of 1N hydrochloric acid and stirred 3 hours at room temperature. The aqueous phase was then reextracted by ethyl acetate (3×200 ml), washed with water (300 ml) and dried over magnesium. The solvent was evaporated under reduced pressure to give 33.2 g of the crude product as a brown oil.

The crude product was purified by flash chromatography on silica gel (eluent: heptane/ethyl acetate 9:1) to give 1-[3-chloro-5-(trifluoromethyl)-2-pyridinyl]ethanone: 13.1 g (40%) as a yellow oil.

Mass spectrum: [M+1]=224.

Preparation of 2-bromo-1-[3-chloro-5-(trifluoromethyl)-2-pyridinyl]ethanone

To a solution of 16.6 g (0.074 mol) of 1-[3-chloro-5-(trifluoromethyl)-2-pyridinyl]ethanone in 150 ml of dry tetrahydrofuran, were added portionwise at room temperature 27.8 g (0.074 mol) of phenyltrimethylammonium tribromide. The solution was stirred for 3 hours at room temperature. The formed solid was removed by filtration and the mother liquors were concentrated under vacuum. The resulting orange oil (32.7 g) was purified by flash chromatography on silica gel (eluent: heptane/dichloromethane 3:1) to give 2-bromo-1-[3-chloro-5-(trifluoromethyl)-2-pyridinyl]ethanone: 10.4 g (46%) as a yellow oil.

Mass spectrum: [M−1]=302.

Preparation of 2-(2-[3-chloro-5-(trifluoromethyl)-2-pyridinyl]-2-oxoethyl)-1H-isoindole-1.3(2H)-dione To a solution of 1 g (3.3 mmol) of 2-bromo-1-[3-chloro-5-(trifluoromethyl)-2-pyridinyl]ethanone in 10 ml of 2-butanone were successively added 50 mg (0.33 mmol) of potassium iodide and 1.23 g (6.6 mmole) of potassium phthalimide. The reaction mixture was stirred at 86° C. for 2 hours. The reaction mixture was poured into 100 ml of water and the aqueous phase was extracted with ethyl acetate (2×50 ml) and the organic phase was washed with water and dried over magnesium sulfate.

The solvent was evaporated under reduced pressure and the resulting solid was triturated in dichloromethane to give 2-{2-[3-chloro-5-(trifluoromethyl)-2-pyridinyl]-2-oxoethyl}-1H-isoindole-1,3(2H)-dione: 0.35 g (29%) as a beige solid; mp=162° C.

Mass spectrum: [M+1]=369.

Preparation of 2-{2-[3-chloro-5-(trifluoromethyl)-2-pyridinyl]-2-hydroxyethyl}-1H-isoindole-1.3(2H)-dione To a suspension of 36 mg (0.95 mmol) of sodium borohydride in 5 ml of methanol, was added at 0° C., 700 mg (1.9 mmol) of 2-{2-[3-chloro-5-(trifluoromethyl)-2-pyridinyl]-2-oxoethyl}-1H-isoindole-1,3(2H)-dione. The reaction mixture was stirred at room temperature for 1 hour. The pH was brought to 7 by addition of 1N hydrochloric acid and methanol was remove under reduced pressure. The residue was reextracted by dichloromethane (2×50 ml) and the organic phase was washed with brine and dried over magnesium sulfate. The solvent was evaporated to give 0.55 g of the crude product as a yellow solid.

The crude product was purified by flash chromatography on silica gel (eluent: heptane/ethyl acetate 8:2) to give 2-{2-[3-chloro-5-(trifluoromethyl)-2-pyridinyl]-2-hydroxyethyl}-1H-isoindole-1,3(2H)-dione: 0.3 g (42%) as a cream-coloured solid.

Mass spectrum: [M+1]=371.

Preparation of 2-amino-1-[3-chloro-5-(trifluoromethyl)-2-pyridinyl]ethanol

To a suspension of 150 mg (0.4 mmol) of 2-{2-[3-chloro-5-(trifluoromethyl)-2-pyridinyl]-2-hydroxyethyl}-M-isoindole-1,3(2H)-dione in 3 ml of ethanol, was added 0.02 ml (0.4 mmol) of hydrazine monohydrate.

The reaction mixture was heated at reflux for 4 hours. After cooling, the white solid was filtered off and the mother liquors were concentrated under vacuum to give 2-amino-1-[3-chloro-5-(trifluoromethyl)-2-pyridinyl]ethanol: 50 mg (52%) as a yellow solid.

Mass spectrum: [M+1]=241.

Examples of Biological Activity of the Compound of General Formula (I)

Example A

In vivo Test on *Alternaria brassicae* (Leaf Spot of Crucifers)

The active ingredient tested is prepared by potter homogenisation in a concentrated suspension type formulation at 100 g/l. This suspension is then diluted with water to obtain the desired active material concentration.

Radish plants (Pernot variety) in starter cups, sown on a 50/50 peat soil-pozzolana substrate and grown at 18-20° C., are treated at the cotyledon stage by spraying with the aqueous suspension described above.

Plants, used as controls, are treated with an aqueous solution not containing the active material.

After 24 hours, the plants are contaminated by spraying them with an aqueous suspension of *Alternaria brassicae* spores (40,000 spores per cm$^3$). The spores are collected from a 12-13-day-old culture.

The contaminated radish plants are incubated for 6-7 days at about 18° C., under a humid atmosphere.

Grading is carried out 6 to 7 days after the contamination, in comparison with the control plants.

Under these conditions, good (at least 50%) to total protection is observed at a dose of 330 ppm with the following compounds: 1, 2, 3, 7, 8, 9, 10, 11, 12, 13, 15, 16, 17, 18, 20, 23, 32, 33, 34, 37, 40, 52, 54 and 58.

Example B

In vivo Test on *Erysiphe graminis* f. sp. *tritici* (Powdery Mildew of Wheat)

The active ingredient tested is prepared by potter homogenisation in a concentrated suspension type formulation at 100 g/l. This suspension is then diluted with water to obtain the desired active material concentration.

Wheat plants (Audace variety) in starter cups, sown on 50/50 peat soil-pozzolana substrate and grown at 12° C., are treated at the 1-leaf stage (10 cm tall) by spraying with the aqueous suspension described above.

Plants, used as controls, are treated with an aqueous solution not containing the active material.

After 24 hours, the plants are contaminated by dusting them with *Erysiphe graminis* f. sp. *tritici* spores, the dusting being carried out using diseased plants. Grading is carried out 7 to 14 days after the contamination, in comparison with the control plants.

Under these conditions, good (at least 50%) to total protection is observed at a dose of 330 ppm with the following compounds: 8, 9, 11, 15, 18, 20 and 23.

Example C

In vivo Test on *Botrytis cinerea* (Cucumber Grey Mould)

The active ingredient tested is prepared by potter homogenisation in a concentrated suspension type formulation at 100 g/l. This suspension is then diluted with water to obtain the desired active material concentration.

Cucumber plants (Marketer variety) in starter cups, sown on a 50/50 peat soil-pozzolana substrate and grown at 18-20° C., are treated at the cotyledon Z11 stage by spraying with the aqueous suspension described above. Plants, used as controls, are treated with an aqueous solution not containing the active material.

After 24 hours, the plants are contaminated by depositing drops of an aqueous suspension of *Botrytis cinerea* spores (150,000 spores per ml) on upper surface of the leaves. The spores are collected from a 15-day-old culture and are suspended in a nutrient solution composed of
20 g/L of gelatin
50 g/L of cane sugar
2 g/L of $NH_4NO_3$
1 g/L of $KH_2PO_4$ The contaminated cucumber plants are settled for 5/7 days in a climatic room at 15-11° C. (day/night) and at 80% relative humidity.

Grading is carried out 5/7 days after the contamination, in comparison with the control plants.

Under these conditions, good (at least 50%) to total protection is observed at a dose of 330 ppm with the following compounds: 12, 24, 31 and 33.

Example D

In vivo Test on *Pyrenophora teres* (Barley Net Blotch)

The active ingredient tested is prepared by potter homogenisation in a concentrated suspension type formulation at 100 g/l. This suspension is then diluted with water to obtain the desired active material concentration.

Barley plants (Express variety) in starter cups, sown on a 50/50 peat soil-pozzolana substrate and grown at 12° C., are treated at the 1-leaf stage (10 cm tall) by spraying with the aqueous suspension described above. Plants, used as controls, are treated with an aqueous solution not containing the active material. After 24 hours, the plants are contaminated by spraying them with an aqueous suspension of *Pyrenophora teres* spores (12,000 spores per ml). The spores are collected from a 12-day-old culture. The contaminated barley plants are incubated for 24 hours at about 20° C. and at 100% relative humidity, and then for 12 days at 80% relative humidity.

Grading is carried out 12 days after the contamination, in comparison with the control plants.

Under these conditions, good (at least 50%) to total protection is observed at a dose of 330 ppm with the following compounds: 2, 4, 7, 8, 9, 11, 12, 14, 15, 16, 17, 18, 20, 21, 22, 23, 24, 25, 29, 32, 33, 34, 37, 40, 50, 51, 52, 53, 54, 56, 57, 58 and 59.

Example E

In vivo Test on *Peronospora brassicae*

The active ingredient tested is prepared by potter homogenisation in a concentrated suspension type formulation at 100 g/l. This suspension is then diluted with water to obtain the desired active material concentration.

Cabbage plants (Eminence variety) in starter cups, sown on a 50/50 peat soil-pozzolana substrate and grown at 18-20° C., are treated at the cotyledon stage by spraying with the aqueous suspension described above. Plants, used as controls, are treated with an aqueous solution not containing the active material.

After 24 hours, the plants are contaminated by spraying them with an aqueous suspension of *Peronospora* brassicae spores (50,000 spores per ml). The spores are collected from infected plant.

The contaminated cabbage plants are incubated for 5 days at 20° C., under a humid atmosphere.

Grading is carried out 5 days after the contamination, in comparison with the control plants.

Under these conditions, good (at least 50%) to total protection is observed at a dose of 330 ppm with the following compounds: 46.

The N-{1-methylcarbamoyl-2-[3-chloro-5-(trifluoromethyl)-2-pyridinyl]-ethyl}-4-phenylbenzamide disclosed by Patent Application WO 01/11965 (see compound 316 in Table D) showed poor effectiveness on *Alternaria brassicae*, and zero effectiveness on *Botrytis cinerea* at 330 ppm; the N-{1-ethylcarbamoyl-2-[3-chloro-5-(trifluoromethyl)-2-pyridinyl]ethyl}-3-nitrobenzamide also disclosed by Patent Application WO 01/11965 (see compound 307 in Table D) showed poor effectiveness on *Alternaria brassicae* and zero effectiveness on *Botrytis cinerea* at 330 ppm; the N-{1-ethylcarbamoyl-2-[3-chloro-5-(trifluoromethyl)-2-pyridinyl]-ethyl}-benzamide and the N-{1-methylcarbamoyl-2-[3-chloro-5-(trifluoromethyl)-2-pyridinyl]ethyl}-benzamide also disclosed by Patent Application WO 01/11965 (see compounds 304 and 314 in Table D) showed zero effectiveness on *Botrytis cinerea* at 330 ppm; and the N-{1-ethylcarbamoyl-2-[3-chloro-5-(trifluoromethyl)-2-pyridinyl]ethyl}-4-chlorobenzamide, the N-{1-ethylcarbamoyl-2-[3-chloro-5-(trifluoromethyl)-2-pyridinyl]ethyl}-2-bromobenzamide and the N-{1-methylcarbamoyl-2-[3-chloro-5-(trifluoromethyl)-2-pyridinyl]ethyl}-4-methoxybenzamide also disclosed by Patent Application WO 01/11965 (see compounds 306, 310 and 315 in Table D) showed zero effectiveness on *Botrytis cinerea* at 330 ppm.

The N-{[3-chloro-5-(trifluoromethyl)-2-pyridinyl]methyl}-5-thienylacetamide disclosed by Patent Application WO 01/11965 (see compound 101 in table B) showed poor efficacy against *Alternaria brassicae* and no efficacy against *Botrytis cinerea* and *Peronospora parasitica* at 330 ppm.

The invention claimed is:
1. A compound of formula (I)

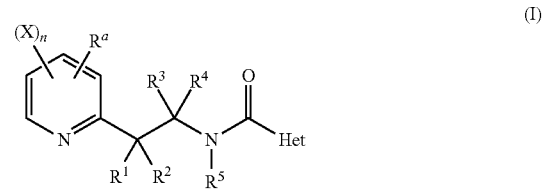

wherein:
n is 1,2 or 3;
$R^a$ is a $C_1$-$C_6$-halogenoalkyl having 1 to 5 halogen atoms;
each substituent X is independently selected from the group consisting of a hydrogen atom, a halogen atom, a $C_1$-$C_6$-alkyl, and a $C_1$-$C_6$-halogenoalkyl;
$R^1$, $R^2$, $R^3$ and $R^4$ are independently selected from the group consisting of a hydrogen atom, a halogen atom, a cyano group, a hydroxy group, an amino group, a sulfanyl group, a formyl group, a formyloxy group, a formylamino group, a carboxy group, a carbamoyl group, a N-hydroxycarbamoyl group, a carbamate group, a (hydroxyimino)-$C_1$-$C_6$-alkyl group, a $C_1$-$C_6$-alkyl, a $C_2$-$C_6$-alkenyl, a $C_2$-$C_6$-alkynyl, a $C_1$-$C_6$-alkylamino, a di-$C_1$-$C_6$-alkylamino, a $C_1$-$C_6$-alkoxy, a $C_1$-$C_6$-halogenoalkyl having 1 to 5 halogen atoms, a $C_1$-$C_6$-halogenoalkoxy having 1 to 5 halogen atoms, a $C_1$-$C_6$-alkylsulfanyl, a $C_1$-$C_6$-halogenoalkylsulfanyl having 1 to 5 halogen atoms, a $C_2$-$C_6$-alkenyloxy, a $C_2$-$C_6$-halogenoalkenyloxy having 1 to 5 halogen atoms, a $C_3$-$C_6$-alkynyloxy, a $C_3$-$C_6$-halogenoalkynyloxy having 1 to 5 halogen atoms, a $C_3$-$C_6$-cycloalkyl, a $C_3$-$C_6$-halogenocycloalkyl having 1 to 5 halogen atoms, a $C_1$-$C_6$-alkylcarbonyl, a $C_1$-$C_6$-halogenoalkylcarbonyl having 1 to 5 halogen atoms, a $C_1$-$C_6$-alkylcarbamoyl, a di-$C_1$-$C_6$-alkylcarbamoyl, a N-$C_1$-$C_6$-alkyloxycarbamoyl, a $C_1$-$C_6$-alkoxycarbamoyl, a N-$C_1$-$C_6$-alkyl-$C_1$-$C_6$-alkoxycarbamoyl, a $C_1$-$C_6$-alkoxycarbonyl, a $C_1$-$C_6$-halogenoalkoxycarbonyl having 1 to 5 halogen atoms, a $C_1$-$C_6$-alkylcarbonyloxy, a $C_1$-$C_6$-halogenoalkylcarbonyloxy having 1 to 5 halogen atoms, a $C_1$-$C_6$-alkylcarbonylamino, a $C_1$-$C_6$-halogenoalkylcarbonylamino having 1 to 5 halogen atoms, a $C_1$-$C_6$-alkylaminocarbonyloxy, a di-$C_1$-$C_6$-alkylaminocarbonyloxy, a $C_1$-$C_6$-alkyloxycarbonyloxy, a $C_1$-$C_6$-alkylsulfenyl, a $C_1$-$C_6$-halogenoalkylsulfenyl having 1 to 5 halogen atoms, a $C_1$-$C_6$-alkylsulfinyl, a $C_1$-$C_6$-halogenoalkylsulfinyl having 1 to 5 halogen atoms, a $C_1$-$C_6$-alkylsulfonyl, a $C_1$-$C_6$-halogenoalkylsulfonyl having 1 to 5 halogen atoms, a benzyl, a benzyloxy, a benzylsulfanyl, a benzylsulfinyl, a benzylsulfonyl, a benzylamino, a phenoxy, a phenylsulfanyl, a phenylsulfinyl, a phenylsulfonyl, a phenylamino, a phenylcarbonylamino, a 2,6 dichlorophenyl-carbonylamino group, and a phenyl group; or $R^1$ and $R^2$ may form together a cyclopropyl, a cyclobutyl, a cyclopentyl or a cyclohexyl;
with the proviso that when three of the four substituents $R^1$, $R^2$, $R^3$ and $R^4$ are a hydrogen atom, then the fourth substituent is not a hydrogen atom;
$R^5$ is selected from the group consisting of a hydrogen atom, a cyano group, a formyl group, a hydroxy group, a $C_1$-$C_6$-alkyl, a $C_1$-$C_6$-halogenoalkyl having 1 to 5 halogen atoms, a $C_1$-$C_6$-alkoxy, a $C_1$-$C_6$-halogenoalkoxy having 1 to 5 halogen atoms, a $C_3$-$C_6$-cycloalkyl, a $C_3$-$C_6$-halogenocycloalkyl having 1 to 5 halogen atoms, a $C_2$-$C_6$-alkenyl, a $C_2$-$C_6$-alkynyl, a $C_1$-$C_6$-alkoxy-$C_1$-$C_6$-alkyl, a $C_1$-$C_6$-cyanoalkyl, a $C_1$-$C_6$-aminoalkyl, a $C_1$-$C_6$-alkylamino-$C_1$-$C_6$-alkyl, a di-$C_1$-$C_6$-alkylamino-$C_1$-$C_6$-alkyl, a $C_1$-$C_6$-alkylcarbonyl, a $C_1$-$C_6$-halogenalkylcarbonyl having 1 to 5 halogen atoms, a $C_1$-$C_6$-alkyloxycarbonyl, a $C_3$-$C_7$-cycloalkyl, a $C_3$-$C_7$-halogenocycloalkyl having 1 to 5 halogen atoms, a $C_3$-$C_7$-cycloalkyl-$C_1$-$C_6$-alkyl, a $C_1$-$C_6$-benzyloxycarbonyl, a $C_1$-$C_6$-alkoxy-$C_1$-$C_6$-alkylcarbonyl, a $C_1$-$C_6$-alkylsulfonyl, and a $C_1$-$C_6$-halogenoalkylsulfonyl having 1 to 5 halogen atoms; and Het is a substituted pyrazole linked by a carbon atom selected from the group consisting of:

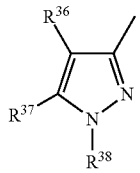

wherein:
$R^{36}$ is selected from the group consisting of a halogen atom, a cyano group, a nitro group, a $C_1$-$C_4$-alkyl, a $C_1$-$C_4$-halogenoalkyl having 1 to 5 halogen atoms, a $C_3$-$C_6$-cycloalkyl, a $C_1$-$C_4$-alkoxy, a $C_1$-$C_4$-halogenoalkoxy having 1 to 5 halogen atoms, a $C_1$-$C_4$-alkylthio, a $C_1$-$C_4$-halogenoalkylthio having 1 to 5 halogen atoms, an aminocarbonyl group, and an aminocarbonyl-$C_1$-$C_4$-alkyl;

$R^{37}$ is selected from the group consisting of a hydrogen atom, a halogen atom, a cyano group, a nitro group, a $C_1$-$C_4$-alkyl, a $C_1$-$C_4$-alkoxy, and a $C_1$-$C_4$-alkylthio; and $R^{38}$ is selected from the group consisting of a hydrogen atom, a phenyl, a $C_1$-$C_4$-alkyl, a $C_1$-$C_4$-halogenoalkyl having 1 to 5 halogen atoms, a hydroxy-$C_1$-$C_4$-alkyl, a $C_2$-$C_6$-alkenyl, a $C_3$-$C_6$-cycloalkyl, a $C_1$-$C_4$-alkylthio-$C_1$-$C_4$-alkyl, a $C_1$-$C_4$-halogenoalkylthio-$C_1$-$C_4$-alkyl having 1 to 5 halogen atoms, a $C_1$-$C_4$-alkoxy-$C_1$-$C_4$-alkyl, and a $C_1$-$C_4$-halogenoalkoxy-$C_1$-$C_4$alkyl having 1 to 5 halogen atoms;

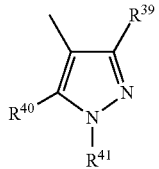

wherein:
$R^{39}$ is selected from the group consisting of a hydrogen atom, a halogen atom, a cyano group, a nitro group, a $C_1$-$C_4$-alkyl, a $C_1$-$C_4$-halogenoalkyl having 1 to 5 halogen atoms, a $C_3$-$C_6$-cycloalkyl, a $C_1$-$C_4$-alkoxy, a $C_1$-$C_4$-halogenoalkoxy having 1 to 5 halogen atoms, a $C_1$-$C_4$-alkylthio, a $C_1$-$C_4$-halogenoalkylthio having 1 to 5 halogen atoms, an aminocarbonyl, and an aminocarbonyl-$C_1$-$C_4$-alkyl;

$R^{40}$ is selected from the group consisting of a hydrogen atom, a halogen atom, a cyano group, a $C_1$-$C_4$-alkyl, a $C_1$-$C_4$-alkoxy, a $C_1$-$C_4$-halogenoalkoxy having 1 to 5 halogen atoms, and a $C_1$-$C_4$-alkylthio; and $R^{41}$ is selected from the group consisting of a hydrogen atom, a $C_1$-$C_4$-alkyl, a $C_1$-$C_4$-halogenoalkyl having 1 to 5 halogen atoms, a hydroxy-$C_1$-$C_4$-alkyl, a $C_2$-$C_6$-alkenyl, a $C_3$-$C_6$-cycloalkyl, a $C_1$-$C_4$-alkylthio-$C_1$-$C_4$-alkyl, a $C_1$-$C_4$-halogenoalkylthio-$C_1$-$C_4$-alkyl having 1 to 5 halogen atoms, a $C_1$-$C_4$-alkoxy-$C_1$-$C_4$alkyl, a $C_1$-$C_4$-halogenoalkoxy-$C_1$-$C_4$-alkyl having 1 to 5 halogen atoms, and a phenyl optionally substituted by a halogen atom, a $C_1$-$C_4$-alkyl, a $C_1$-$C_4$-alkoxyalkyl or a nitro group;

provided that the $R^{39}$ and $R^{40}$ are not both a hydrogen atom; and

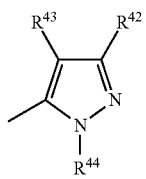

wherein:
$R^{42}$ is selected from the group consisting of a hydrogen atom, a halogen atom, a cyano group, a nitro group, a $C_1$-$C_4$-alkyl, a $C_1$-$C_4$-halogenoalkyl having 1 to 5 halogen atoms, a $C_3$-$C_6$-cycloalkyl, a $C_1$-$C_4$-alkoxy, a $C_1$-$C_4$-halogenoalkoxy having 1 to 5 halogen atoms, a $C_1$-$C_4$-alkylthio, a $C_1$-$C_4$-halogenoalkylthio having 1 to 5 halogen atoms, an aminocarbonyl, and an aminocarbonyl-$C_1$-$C_4$-alkyl;

$R^{43}$ is selected from the group consisting of a hydrogen atom, a halogen atom, a cyano group, a $C_1$-$C_4$-alkyl, a $C_1$-$C_4$-alkoxy, a $C_1$-$C_4$-alkylthio, and a $C_1$-$C_4$-halogenoalky having 1 to 5 halogen atoms;

$R^{44}$ is selected from the group consisting of a hydrogen atom, a phenyl, a benzyl, a $C_1$-$C_4$-alkyl, a $C_1$-$C_4$-halogenoalkyl having 1 to 5 halogen atoms, a hydroxy-$C_1$-$C_4$-alkyl, a $C_2$-$C_6$-alkenyl, a $C_3$-$C_6$-cycloalkyl, a $C_1$-$C_4$-alkylthio-$C_1$-$C_4$-alkyl, a $C_1$-$C_4$-halogenoalkylthio-$C_1$-$C_4$-alkyl having 1 to 5 halogen atoms, a $C_1$-$C_4$-alkoxy-$C_1$-$C_4$-alkyl, and a $C_1$-$C_4$-halogenoalkoxy-$C_1$-$C_4$-alkyl having 1 to 5 halogen atoms;

provided that $R^{43}$ and $R^{44}$ are not both a hydrogen atom; or a salt, N-oxide, or optically active isomer thereof.

2. The compound of claim 1 wherein n is 1 or 2.

3. The compound of claim 1 wherein X is a halogen atom.

4. The compound of claim 3 wherein X is chlorine.

5. The compound of claim 1 wherein $R^a$ is —$CF_3$.

6. The compound of claim 1 wherein the 2-pyridyl is substituted in the 3- and/or in the 5-position.

7. The compound of claim 6 wherein the 2-pyridyl is substituted in the 3-position by X and in the 5-position by $R^a$.

8. The compound of claim 1 wherein the 2-pyridyl is substituted in the 3-position by —Cl and in the 5-position by —$CF_3$.

9. The compound of claim 1 wherein $R^1$ and $R^2$ are independently selected from the group consisting of a hydrogen atom, a halogen atom, a cyano group, a hydroxy group, a $C_1$-$C_6$-alkyl, a $C_1$-$C_6$-halogenoalkyl having 1 to 5 halogen atoms, a $C_2$-$C_6$-alkenyl, a $C_1$-$C_6$-alkoxy, a $C_1$-$C_6$-alkylsulfanyl, a $C_1$-$C_6$-alkylsulfenyl, a $C_1$-$C_6$-alkylsulfinyl, a $C_1$-$C_6$-alkoxycarbonyl, a $C_1$-$C_6$-alkylcarbonylamino, a $C_1$-$C_6$-alkoxycarbonyloxy, a $C_1$-$C_6$-alkoxycarbonylamino, and a phenyl group.

10. The compound of claim 9 wherein $R^1$ and $R^2$ are independently selected from the group consisting of a halogen atom, a $C_1$-$C_6$-alkyl, a $C_1$-$C_6$-halogenoalkyl having 1 to 5 halogen atoms, and a $C_1$-$C_6$-alkylcarbonylamino.

11. The compound of claim 1 wherein $R^3$ and $R^4$ are independently selected from the group consisting of a hydrogen atom, a halogen atom, a cyano group, a $C_1$-$C_6$-alkyl, a $C_1$-$C_6$-halogenoalkyl having 1 to 5 halogen atoms, a $C_1$-$C_6$-alkylcarbonylamino, and a phenyl group.

12. The compound of claim 11 wherein $R^3$ and $R^4$ are independently selected from the group consisting of a halogen atom, a $C_1$-$C_6$-alkyl, a $C_1$-$C_6$-halogenoalkyl having 1 to 5 halogen atoms, and a phenyl group.

13. The compound of claim 1 wherein $R^5$ is selected from the group consisting of a hydrogen atom, and a $C_3$-$C_7$-cycloalkyl.

14. A fungicidal composition comprising an effective amount of the compound of claim 1 and an agriculturally acceptable support.

15. A method for combating the phytopathogenic fungi of crops comprising applying an effective and non-phytotoxic amount of a composition according to claim 14 to the plant seeds or to the plant leaves and/or to the fruits of the plants or to the soil in which the plants are growing or in which it is desired to grow them.

16. A compound of the structural formula:

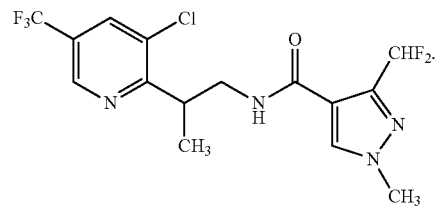

17. A fungicidal composition comprising an effective amount of the compound of claim 16 and an agriculturally acceptable support.

18. A method for combating the phytopathogenic fungi of crops comprising applying an effective and non-phytotoxic amount of a composition according to claim 17 to the plant seeds or to the plant leaves and/or to the fruits of the plants or to the soil in which the plants are growing or in which it is desired to grow them.

* * * * *